(12) United States Patent
Deslongchamps et al.

(10) Patent No.: US 9,409,945 B2
(45) Date of Patent: *Aug. 9, 2016

(54) COMBINATORIAL SYNTHESIS OF LIBRARIES OF MACROCYCLIC COMPOUNDS USEFUL IN DRUG DISCOVERY

(71) Applicant: OCERA THERAPEUTICS, INC., Palo Alto, CA (US)

(72) Inventors: Pierre Deslongchamps, Sherbrooke (CA); Yves Dory, Cookshire (CA); Gilles Berthiaume, Quebec (CA); Luc Ouellet, Sherbrooke (CA); Ruoxi Lan, Arlington, MA (US)

(73) Assignee: Ocera Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,742

(22) Filed: Apr. 27, 2015

(65) Prior Publication Data

US 2015/0315235 A1    Nov. 5, 2015

Related U.S. Application Data

(63) Continuation of application No. 13/218,784, filed on Aug. 26, 2011, now Pat. No. 9,018,419, which is a continuation of application No. 11/615,332, filed on Dec. 22, 2006, now Pat. No. 8,008,440, which is a continuation of application No. 09/679,331, filed on Oct. 4, 2000, now Pat. No. 7,169,899.

(30) Foreign Application Priority Data

Oct. 4, 1999   (CA) ...................... 2284459

(51) Int. Cl.

| | |
|---|---|
| C07D 255/02 | (2006.01) |
| C07D 245/02 | (2006.01) |
| C07K 5/083 | (2006.01) |
| C07K 5/08 | (2006.01) |
| C07K 1/04 | (2006.01) |
| C07K 5/09 | (2006.01) |
| C07K 5/093 | (2006.01) |
| C07K 7/54 | (2006.01) |
| C07K 7/64 | (2006.01) |
| C40B 40/00 | (2006.01) |

(52) U.S. Cl.
CPC ............... *C07K 5/0808* (2013.01); *C07K 1/04* (2013.01); *C07K 1/047* (2013.01); *C07K 5/08* (2013.01); *C07K 5/081* (2013.01); *C07K 5/0806* (2013.01); *C07K 5/0815* (2013.01); *C07K 5/0817* (2013.01); *C07K 5/0819* (2013.01); *C07K 7/54* (2013.01); *C07K 7/64* (2013.01); *C07B 2200/11* (2013.01); *C40B 40/00* (2013.01); *Y10S 930/27* (2013.01)

(58) Field of Classification Search
CPC ........ C07K 5/0808; C07K 1/04; C07K 1/047; C07K 5/08; C07K 5/0806; C07K 5/0815; C07K 5/0817; C07K 7/54
USPC ............. 530/321, 323, 331, 332, 371; 514/18
See application file for complete search history.

(56) References Cited

U.S. PATENT DOCUMENTS

| | | | |
|---|---|---|---|
| 4,252,951 A | 2/1981 | Jackson et al. | |
| 5,635,477 A | 6/1997 | Degrado | |
| 6,107,275 A | 8/2000 | Harbeson | |
| 6,235,877 B1 | 5/2001 | Scolastico et al. | |
| 6,355,613 B1 * | 3/2002 | Hornik ........... | G01R 31/318541 514/11.1 |
| 6,437,094 B2 | 8/2002 | Scolastico et al. | |
| 6,864,244 B2 | 3/2005 | Connolly et al. | |
| 7,169,899 B1 | 1/2007 | Deslongchamps et al. | |
| 7,521,420 B2 | 4/2009 | Fraser et al. | |
| 8,008,440 B2 * | 8/2011 | Deslongchamps ...... | C07K 1/04 530/321 |
| 9,018,419 B2 * | 4/2015 | Deslongchamps ...... | C07K 1/04 564/305 |
| 2005/0049234 A1 | 3/2005 | Deslongchamps et al. | |

FOREIGN PATENT DOCUMENTS

| | | |
|---|---|---|
| JP | 6-505486 | 6/1994 |
| JP | 10-512570 | 12/1998 |
| JP | 2003511387 A | 3/2003 |
| JP | 5005865 B2 | 8/2012 |
| WO | WO 92/13878 | 8/1992 |
| WO | WO 92/13878 A2 | 8/1992 |
| WO | WO 96/22304 | 7/1996 |
| WO | WO 96/22304 A1 | 7/1996 |
| WO | WO 96-22304 A1 | 7/1996 |
| WO | WO 98/46631 A1 | 10/1998 |
| WO | WO 99/48913 A1 | 9/1999 |
| WO | WO 01/25257 A2 | 4/2001 |
| WO | WO-03/059876 A2 | 7/2003 |
| WO | WO-03/059933 A2 | 7/2003 |

OTHER PUBLICATIONS

Fornasier et al. "Bolaform and Classical Cationic Metallomicelles as Catalysts of the Cleavage of p-Nitrophenyl Picolinate", *J. Am. Chem. Soc.* 111:224-229 (1989).

Perlman et al. "Epoxidation of Peptidyl Olefin Isosteres. Stereochemical Induction Effect of Chiral Centers at Four Adjacent $C_\alpha$ Positions", *Tetrahedron* 56:1505-1516 (2000).

"Protecting Group Stability", chart printed from http://www.organic-chemistry.org/.

Take et al. "Agents for the Treatment of Overactive Detrusor. III. Synthesis and Structure-Activity Relationships of N-(4-Amino-2-butynyl)acetamide Derivatives", *Chem. Pharm. Bull.* 40(6):1415-1423 (1992).

Kessler, Horst; Diefenbach, Beate; Finsinger, Dirk; Geyer, Armin; Gurrath, Marion; Goodman, Simon L.; Höelzemann, Günter; Haubner, Roland; Jonczyk, Alfred; et al. Design of Superactive and Selective integrin receptor antagonists containing the RGD sequence. *Letters in Peptide Science* 1995, 2, 155-160.

Gonzalez, Jesus E., et al., "Cell-based assays and instrumentation for screening ion-channel targets", Drug Discov. Today, vol. 4, No. 9, Sep. 1999, pp. 431-439.

Ramm, Peter, "Imaging systems in assay screening", Drug Discov, Today, vol. 4, No. 9, Sep. 1999, pp. 401-410.

Gonzalez, Jesus E., et al., "Intracellular detection assays for high-throughput screening", Curr. Opin. Biotechnol., Dec. 1998, vol. 9, No. 6, pp. 624-631.

Fernandes, Prabhavathi B., "Technological advances in high-throughput screening", Curr. Opin. Chem. Biol., Oct. 1998, vol. 2, No. 5, pp. 597-603.

Silverman, Lauren, et al., "New assay technologies for high-throughput screening", Curr. Opin. Chem. Blol., Jun. 1998, vol. 2, No. 3, pp. 397-403.

Houston, John G., et al., "The chemical-biological interface: developments in automated and miniaturised screening technology", Curr. Opin. Biotechnol. Dec. 1997, vol. 8, No. 6, pp. 734-740.

Pausch, Mark H., "G-protein-coupled receptors in *Saccharomyces cervisiae*: high-throughput screening assays for drug discovery", Trends Biotechnol., Dec. 1997, vol. 15, pp. 487-494.

Stewart, John Morrow, et al., "Solid Phase Peptide Synthesis", Pierce Chemical Co., Rockford, IL, 1984, pp. 14-28 (protecting groups).

Bodanszky, Miklos, "Principles of Peptide Synthesis", Springer-Verlag, New York, 1993, p. 215-218 (amino and carboxyl protection).

Albericio, Fernando, "Orthogonal Protecting Groups for Nα-Amino and C-Terminal Carboxyl Functions in Solid-Phase Peptide Synthesis", Biopolymers (Peptide Science), vol. 55, 2000, pp. 123-139.

Yokum, T. Scott, et al., "Strategy in Solid-Phase Peptide Synthesis", Solid-Phase Synthesis: A practical Guide, Kates, Steven A., et al., eds., Marcel Dekker, Inc., New York, 2000, pp. 79-102.

Wade, John D., "Amino Acids: Alpha-Amino Protecting Groups", Solid-Phase Synthesis: A practical Guide, Kates, Steven A., et al., eds., Marcel Dekker, Inc., New York, 2000, pp. 103-128.

Doherty-Kirby, Amanda L., et al., "Side-Chain Protecting Groups", Solid-Phase Synthesis: A practical Guide, Kates, Steven A., et al., eds., Marcel Dekker, Inc., New York, 2000, pp. 129-195.

Chan, Weng C., et al., "Fmoc solid phase peptide synthesis: A Practical Approach", Oxford University Press, New York, 2000, pp. 20-26 (protecting groups).

Barany, George, et al., A New Amino Protecting Group Removable by Reduction. Chemistry of the Dithiasuccinoyl (Dts) Function), J. Am. Chem. Soc., 1997, vol. 99, pp. 7363-7365, footnote 4.

Lloyd-Williams, et al., "Convergent solid-phase peptide synthesis", 1993, Tetrahedron, vol. 49, No. 48, pp. 11065-11133.

Parsons, J.A., Peptide Hormones, 1976, University Park Press, London, pp. 1-6.

Adam et al., "Muramyl Peptides: Immunomodulators, Sleep Factors, and Vitamins," Med. Res. Rev. 4:111-152 (1984).

Ashmarin et al., "The neurotropic activity of a structural analog of ACTH(5-7)," Regulatory Peptides 51:49-54 (1994).

Bitan et al., "Backbone Cyclization of the C-terminal Part of Substance P. Part 1: The Important Role of the Sulphur in Position 11," J. Pept. Sci. 2:261-269 (1996).

Blaschuk et al., "Identification of a Cadherin Cell Adhesion Recognition Sequence," Dev. Biol. 139:227-229 (1990).

Boldyrev et al., "The Histidine-Containing Dipeptides, Carnosine and Anserine: Distribution, Properties and Biological Significance," Adv. Enzyme Regul. 30:175-194 (1990).

Bourin et al., "Two faces of cholecystokinin: anxiety and schizophrenia," Fundam. Clin. Pharmacol. 10:116-126 (1996).

Broadbridge et al., "The Src Homology-2 Domains (SH2 Domains) of the Protein Tyrosine Kinase $p56^{lck}$: Structure, Mechanism and Drug Design," Curr. Drug Targets 1:365-386 (2000).

Burger et al., "Enzymatic, Polymer-Supported Formation of an Analog of the Trypsin Inhibitor A90720A: A Screening Strategy for Macrocyclic Peptidase Inhibitors," J. Am. Chem. Soc. 119:12697-12698 (1997).

Cho et al., "Cyclic and Linear Oligocarbamate Uganda for Human Thrombin," Bioorg. Med. Chem. 7:1171-1179 (1999).

Cho et al., "Synthesis and Screening of Linear and Cyclic Oligocarbamate Libraries. Discovery of High Affinity Ligands for GPIIb/IIIa," J. Am. Chem. Soc. 120:7706-7718 (1998).

Clements et al., "Identification of a key integrin-binding sequence in VCAM-1 homologous to the LDV active site in fibronectin," J. Cell Sci. 107:2127-2135 (1994).

Cutuli et al., "Antimicrobial effects of α-MSH peptides," J. Leukoc. Biol. 67:233-239 (2000).

Eichler et al., "Cyclic peptide template combinatorial libraries: synthesis and identification of chymotrypsin inhibitors," Pept. Res. 7:300-307 (1994).

Eichler et al.,"Novel α-glucosidase inhibitors identified using multiple cyclic peptide combinatorial libraries," Mol. Divers, 1:233-240 (1995).

Fairlie et al., "Macrocyclic peptidomimetics—forcing peptides into bioactive conformations," Curr. Med, Chem, 2:654-86 (1995).

Feng at al, "Solid-Phase $S_NAr$ Macrocyclizations to Give Turn-Extended-Turn Peptidomimetics," Chem. Eur. J. 5:3261-3272 (1999).

Frolova et al., "Mutations in the highly conserved GGQ motif of class 1 polypeptide release factors abolish ability of human eRF1 to trigger peptidyl-tRNA hydrolysis," RNA 5:1014-1020 (1999).

Fujii et al., "Antimetastatic Activities of Synthetic Arg-Gly-Asp-Ser (RGDS) and Arg-Leu-Asp-Ser (RLDS) Peptide Analogues and Their Inhibitory Mechanisms," Biol. Pharm. Bull. 18:1681-1688 (1995).

Gilon et al., "Backbone Cyclization: A New Method for Conferring Conformational Constraint on Peptides," Biopolymers 31:745-750 (1991).

Glassman et al., "Clinical Pharmacology of Enalkiren, A Novel, Dipeptide Renin Inhibitor," J. Cardiovasc. Pharmacol. 16(Suppl. 4):S76-S81 (1990).

Gould et al., "A Conserved Tripeptide Sorts Proteins to Peroxisomes," J. Cell Biol. 108:1657-1664 (1989).

Greco et al., "Macrocyclic Inhibitors of Serine Proteases," Adv. Amino Acid Mimetics Peptidomimetics, 1:41-76 (1997).

Guan et al., "The Effects of the N-Terminal Tripeptide of Insulin-Like Growth Factor-1, Glycine-Proline-Glutamate in Different Regions Following Hypoxic-Ischemic Brain Injury in Adult Rats," Neuroscience 89:649-659 (1999).

Guerrini et al., "Structure-activity relationships of nociceptin and related peptides: comparison with dynorphin A," Peptides 21:923-933 (2000).

Hiltz et al., "Antiinflammatory activity of a COOH-terminal fragment of the neuropeptide α-MSH," FASEB J 3:2282-2284 (1989).

Hiroshige et al., "Palladium-Mediated Macrocyclization on Solid Support and Its Applications to Combinatorial Synthesis," J. Am. Chem. Soc. 117:11590-11591 (1995).

Houghten, "Soluble Combinatorial Libraries: Extending the Range and Repertoire of Chemical Diversity," Methods: A Companion to Methods in Enzymology 6:354-360 (1994).

Hoveyda et al., "Optimization of the[potency and pharmacokinetic properties of a macrocyclic ghrelin redeptor agonist (Part I): Development of ulimorelin (TZP-101) from hit to clinic," J. Med. Chem. 54:8305-8320 (2011).

Kaiser et al., "Pharmacology of Synthetic Thrombin Inhibitors of the Tripeptide Type," Cardiovasc. Drug Rev. 10:71-87 (1992).

Kamatani et al., "Isolation of Achatin-I, A Neuroactive Tetrapeptide having a D-Phenylalanine Residue, from *Achatina* Ganglia, and Its Effects on *Achatina* Giant Neurones," Comp. Biochem. Physiol. 98C:97-103 (1991).

Kasher et al., "Miniaturized Proteins: The Backbone Cyclic Proteinomimetic Approach," J. Mol. Biol. 292:421-429 (1999).

Katz, "Streptavidin-binding and -dimerizing ligands discovered by phage display, topochemistry, and structure-based design," Biomol. Eng. 16:57-65 (1999).

Kisselev et al., "Translational termination comes of age," Trends Biol. Sci. 25:561-566 (2000).

Komoriya et al., "The Minimal Essential Sequence for a Major Cell Type-specific Adhesion Site (CS1) within the Alternatively Spliced Type III Connecting Segment Domain of Fibronectin Is Leucine-Aspartic Acid-Valine," J. Biol. Chem. 266:23:15075-15079 (1991).

Kuriyan et al., "Modular Peptide Recognition Domain's in Eukaryotic Signaling," Annu. Rev. Biophys. Biomol. Struct. 26:259-288 (1997).

Lee et al., "A Strategy for Macrocyclic Ring Closure and Functionalization Aimed toward Split-Pool Syntheses," J. Am. Chem. Soc. 121:10648-10649 (1999).

Lee, "Five years' experience with γ-L-glutamyl-L-dopa: a relatively renally specific dopaminergic prodrug in man," J. Auton. Pharmacol. 10:s103-s108 (1990).

Loosen, "TRH: Behavioral and Endocrine Effects in Man," Prog. Neuro-Psychopharmacol. Biol. Psychiat. 12:S87-S117 (1988).

Maquart et al., "In Vivo Stimulation of Connective Tissue Accumulation by the Tripeptide-Copper Complex Glycyl-L-histidyl-L-lysine-$Cu^{2+}$ in Rat Experimental Wounds," J. Clin. Invest. 92:2368-2376 (1993).

March et al., "Substrate-based cyclic peptidomimetics of Phe-Ile-Val that inhibit HIV-1 protease using a novel enzyme-binding mode," J. Am. Chem. Soc. 118:3375-3379 (1996).

Marsault et al., "Discovery of a new class of macrocyclic antagonists to the human motilin receptor," J. Med. Chem. 49:7190-7197 (2006).

Mathison et al., "Attenuation of Intestinal and Cardiovascular Anaphylaxis by the Salivary Gland Tripeptide FEG and Its D-isomeric Analog feG," Peptides 19:1037-1042 (1998).

McBride at al., "Selection of Chymotrypsin Inhibitors from a Conformationally-constrained Combinatorial Peptide Library," J. Mol. Biol. 259:819-827 (1996).

McGeary et al., "Macrocyclic peptidonnimetics; potential for drug development," Curr. Opin. Drug Discov. Devel. 1998, 1:208-217 (1998).

Meo et al., "Monoclonal antibody to the message sequence Tyr-Gly-Gly-Phe of opioid peptides exhibits the specificity requirements of mammalian opioid receptors," Proc. Nat. Acad. Sci. USA 80:4084-4088 (1983).

Mishra et al., "Pharmacology of L-Prolyl-L-Leucyl-Glycinamide (PLG): A Review," Meth. Find. Exp. Clin. Pharmacol. 5:203-233 (1983).

Myers, "Neuroactive peptides: unique phases in research on mammalian brain over three decades," Peptides 15:367-381 1994.

Nishioka et al., "Tuftsin: A Hormone-Like Tetrapeptide with Antimicrobial and Antitumor Activities," Life Sci. 28:1081-1090 (1981).

Pacofsky et al., "Potent Dipeptide Inhibitors of the $pp60^{c-src}$ SH2 Domain," J. Med. Chem. 41:1894-1908 (1998).

Polanski et al., "Muramyl Peptides as Paradigms in Neuroimmunomodulation," Ann N Y Acad Sci. 650:218-220 (1992).

Prasad, "Cyclo(His-Pro): its distribution, origin and function in the human," Neurosci. Biobehav. Rev. 12:19-22 (1988).

Prasad, "Bioactive byciic Dipeptides," Peptides 16:151-164 (1995).

Quinn et al., "Carnosine: Its Properties, Functions and Potential Therapeutic Applications," Molec. Aspects Med. 13:379-444 (1992).

Raffa, "The Action of FMRFamide (Phe-Met-Arg-Phe-$NH_2$) and Related Peptides on Mammals," Peptides 9:915-922 (1988).

Rao et al., "Three Highly Constrained Tricyclic Peptide Libraries Containing Three Disulfide Bonds," Peptides: Chemistry, Structure and Biology, Pravin TP. Kaumaya and Robert S. Hodges (Eds.) Proc.14.APS. (pp. 299-300). Mayflower Scientific Ltd. Kingswinford (1996).

Ross, "Glutathione, Free Radicals and Chemotherapeutic Agents," Pharmac. Ther. 37:231-249 (1988).

Sara et al., "The Biological Role of Truncated Insulin-like Growth Factor-1 and the Tripeptide GPE in the Central Nervous System," Ann N Y Acad Sci. 692:183-191 (1993).

Saura et al., "Neuroprotective effects of Gly-Pro-Glu, the N-terminal tripeptide of IGF-1, in the hippocampus in vitro," NeuroReport 10:161-164 (1999).

Song et al., "The Crystal Structure of Human Eukaryotic Release Factor eRF1—Mechanism of Stop Codon Recognition and Peptidyl-tRNA Hydrolysis," Cell 100:311-321 (2000).

Spatola et al., "Expanding molecular diversity with pseudopeptides and macrotorials: Synthesis, characterization, and biological activities of macrocyclic combinatorial libraries," American Peptide Symposia vol. 5, Session I, pp. 28-30 (2002).

Spatola at al., "Rediscovering an Endothelin Antagonist (BQ-123): A Self-Deconvoluting Cyclic Pentapeptide Library," J. Med. Chem. 39:3842-3846 (1996).

Spatola et al., "Cyclic Peptide Libraries," Peptides: Chemistry, Structure and Biology, Pravin T.P. Kaumaya and Robert S. Hodges (Eds.) (pp. 281-283) Mayflower Scientific Ltd. (1996).

Spatola at al., "Macrocycles and molecular diversity: a systematic approach," Peptides, Proceedings EPS 1994, pp. 96-97.

Stankovic et al, "Peptidomimetic ligands for SRC Homology-2 domains," Adv. Amino Acid Mimetics Peptidomimetics 1:127-163 (1997).

Tumelty et al., "Synthesis of Head-to-tail and Lactam Cyclized Peptide Libraries," Peptides: Chemistry, Structure and Biology, Pravin T.P. Kaumaya and Robert S. Hodges (Eds.) (pp. 121-122) Mayflower Scientific Ltd. (1996).

Waltho et al., "The natural design of vancomycin family antibiotics to bind their target peptides," Host-Guest Molecular Interactions: From Chemistry to Biology, No. 158 CIBA Foundation Symposium pp. 73-91 (1991).

Wells et al., "The Molecular Basis of the Chemokine/Chemokine Receptor Interaction-Scope for Design of Chemokine Antagonists," Methods: A Companion to Methods in Enzymology 10:126-134 (1996).

Winkler et al., "Determination of the Binding Conformation of Peptide Epitopes Using Cyclic Peptide Libraries," Peptides: Chemistry, Structure and Biology, Pravin T.P. Kaumaya and Robert S. Hodges (Eds.) (pp. 315-316) Mayflower Scientific Ltd. 1996.

Zhang et al., "Novel concepts for the synthesis of cyclic peptide libraries," Am. Peptide Symposia, 2002, vol. 5, Session I, pp. 19-21.

Final Notice of Rejection corresponding to Japanese Application No. 2001-528200 dated Dec. 15, 2011.

Said-Nejad et al. "14-Membered cyclic opioids related to dermorphin and their partially retro-inverso modified analogues", *Int. J. Peptide Protein Res.* 39:145-160 (1992).

Kessler et al., "Design of Superactive and Selective integrin receptor antagonists containing the RGD sequence" *Letters in Peptide Science* 2:155-160 (1995).

Parsons, J.A., "Peptide Hormones", *University Park Press*, London pp. 1-6 (1976).

Samanen et al., "Development of a Small RGD Peptide Fibrinogen Receptor Antagonist with Potent Antiaggregatory Activity in Vitro", *J. Med. Chem.* 34:3114-3125 (1991).

Mihara et al., "Efficient Preparation of Cyclic Peptide Mixtures by Solid Phase Synthesis and Cyclization Cleavage with Oxime Resin" *Tetrahedron Letters* 36(27):4837-4840 (1995).
Kessler et al. "Design of superactive and selective integrin receptor antagonists containing the RGD sequence" *Letters in Peptide Science* 2:155-160 (1995).
Maurin et al. "A Novel Isolation Method of a Stable Crystalline Salt of a Cyclic RGD Peptide Zwitterion[1]", *Pharmaceutical Research* 12(11):1810-1812 (1995).
Canadian Office Action corresponding to Canadian Patent No. 2284459 dated Jun. 5, 2009.
Dolle "Comprehensive survey of chemical libraries yielding enzyme inhibitors, receptor agonists and antagonists, and other biologically active agents: 1992 through 1997", *Molecular Diversity* 3:199-233 (1998).
Dolle "Comprehensive survey of combinatorial libraries with undisclosed biological activity: 1992-1997", *Molecular Diversity* 4:233-256 (1998).
Burger et al. "Enzymatic, Polymer-Supported Formation of an Analog of the Trypain Inhibitor A90720A: A Screening Strategy for Macrocyclic Peptidase Inhibitors", *J. Am. Chem. Soc.* 119:12697-12698 (1997).
Japanese Office Action corresponding to Japanese Application No. 2001-528200 mailed Jun. 8, 2010.
Adam et al, "Muramyl Peptides: Immunomodulators, Sleep Factors, and Vitamins," Med. Res. Rev. 4:111-152 (1984).
Bitan et al., "Backbone Qyclization of the C-terminal Part of Substance P. Part 1: The Important Role of the Sulphur in Position 11," J. Pept, Sci. 2:261-269 (1996).
Burger et al., "Enzymatic, Polymer-Supported Formation of an Analog of the Trypsin Inhibitor A90720A: A Screening Strategy for Macrocyclic Peptidase Inhibitors," J. Am, Chem, Soc. 119:12697-12698 (1997).
Cho et al., "Cyclic and Linear Oligocarbamate Ligands for Human Thrombin," Bioorg, Med. Chem. 7:1171-1179 (1999).
Cho et al., "Synthesis and Screening of Linear and Cyclic Oligocarbamate Libraries, Discovery of High Affinity Ligands for GPIIb/IIIa," J, Am. Chem. Soc. 120:7706-7718 (1998).
Clements et al., "Identification of a key integrin-binding sequence in VCAM-1 homologous to the LDV active site in fibronectin," J. Cell Sci, 107:2127-2135 (1994).
Eichler et al.,"Novel α-glucosidase inhibitors identified using multiple cyclic peptide combinatorial libraries," Mol. Divers. 1:233-240 (1995).
Fairlie et al., "Macrocyclic peptidomimetics—forcing peptides into bioactive conformations," Curr. Med, Chem. 2:654-86 (1995).
Feng et al., "Solid-Phase $S_NAr$ Macrocyclizations to Give Turn-Extended-Turn Peptidomimetics," Chem, Eur. J. 5;3261-3272 (1999).
Frolova et al., "Mutations in the highly conserved GGQ motif of class 1 polypeptide release factors abolish ability of human eRF1 to trigger peptidyl-tRNA hydrolysis," RNAa 5:1014-1020(1999).
Fujii et al., "Antimetastatic Activities of Synthetic Arg-Gly-Asp-Ser (RGDS) and Arg-Leu-Asp-Ser (RLDS) Peptide Analogues and Their Inhibitory Mechanisms," Biol. Pharm. Bull. 18;1681-1688 (1995).
Gi Lon et al., "Backbone Cyclization: A New Method for Conferring Conformational Constraint on Peptides," Biopolymers 31;745-750 (1991).
Glassman et al., "Clinical Pharmacology of Enalkiren, A Novel, Dipeptide Renin Inhibitor," J. Cardiovasc, Pharmacol. 16(Suppl. 4):S76-S81 (1990).
Hiltz et al, "Antiinflammatory activity of a COOH-terminal fragment of the neuropeptide α-MSH," FASEB J 3:2282-2284 (1989).
Kamatani et al., "Isolation of Achatin-I, A Neuroactive Tetrapeptide having a D-Phenylalanine Residue, from *Achatina* Ganglia, and Its Effects on *Achatina* Giant Neurones," Comp. Blochem. Physiol. 98C:97-103 (1991).
Kuriyan et al., "Modular Peptide Recognition Domains in Eukaryotic Signaling," Annu. Rev. Biophys. Biomol. Struct. 26:259-288 (1997).

Maquart et al., "In Vivo Stimulation of Connective Tissue Accumulation by the Tripeptide-Copper Complex Glycyl-L-histidyl-L-lysine-$Cu^{2+}$ in Rat Experimental Wounds," J. Clin. Invest. 92:2368-2376 (1993).
McBride et al., "Selection of Chymotrypsin Inhibitors from a Conformationally-constrained Combinatorial Peptide Library," J. Mol. Biol. 259:819-827 (1996).
McGeary et al., "Macrocyclic peptidomimetics: potential for drug development," Curr. Opin. Drug Discov. Devel. 1998, 1:208-217 (1998).
Myers, "Neuroactive peptides: unique phases in research on mammalian brain over three decades," Peptides 15:367-381 (1994).
Prasad, "Bioactive Cyclic Dipeptides," Peptides 16:151-164 (1995).
Quinn et al,, "Carnosine: Its Properties, Functions and Potential Therapeutic Applications," Molec. Aspects Med. 13:379-444 (1992).
Rao et al., "Three Highly Constrained Tricyclic Peptide Libraries Containing Three Disulfide Bonds," Peptides: Chemistry, Structure and Biology, Pravin TP. Kaumaya and Robert S. Hodges (Eds.) Proc.14.APS. (pp. 299-300). Mayflower Scientific Ltd., Kingswinford (1996).
Spatola et al., "Rediscovering an Endothelin Antagonist (BQ-123): A Self-Deconvoluting Cyclic Pentapeptide Library," J. Med, Chem. 39:3842-3846 (1996).
Spatola et al., "Cyclic Peptide Libraries," Peptides: Chemistry, Structure and Biology, Pravin T.P. Kaumaya and Robert S, Hodges (Eds.) (pp. 281-283) Mayflower Scientific Ltd. (1996).
Spatola et al., "Macrocycles and molecular diversity: a systematic approach," Peptides, Proceedings EPS 1994, pp. 96-97.
Stankovic et al., "Peptidomimetic ligands for SRC Homology-2 domains," Adv. Amino Acid Mimetics Peptidomimetics 1:127-163 (1997).
Winkler et al., "Determination of the Binding Conformation of Peptide Epitopes Using Cyclic Peptide Libraries," Peptides: Chemistry, Structure and Biology, Pravin T.P. Kaumaya and Robert S. Hodges (Eds.) (pp. 315-316) Mayflower Scientific Ltd. (1996).
First Office Action corresponding to Japanese Application No. 2011-179715 mailed Sep. 17, 2013.
First Office Action corresponding to Japanese Application No. 2012-049644 mailed Jan. 7, 2014.

* cited by examiner

*Primary Examiner* — Kamal Saeed
*Assistant Examiner* — Janet L Coppins
(74) *Attorney, Agent, or Firm* — Myers Bigel & Sibley, P.A.

(57) ABSTRACT

A library of macrocyclic compounds of the formula (I)

where part (A) is a

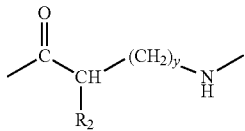

bivalent radical, a —$(CH_2)_y$— bivalent radical or a covalent bond;

where part (B) is a

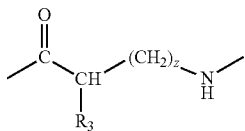

bivalent radical, a —$(CH_2)_z$— bivalent radical, or a covalent bond;

where part (C) is a

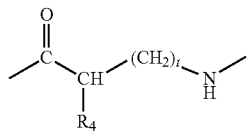

bivalent radical, a —$(CH_2)_t$— bivalent radical, or a covalent bond; and where part (T) is a —Y-L-Z— radical wherein Y is $CH_2$ or CO, Z is NH or O and L is a bivalent radical. These compounds are useful for carrying out screening assays or as intermediates for the synthesis of other compounds of pharmaceutical interest. A process for the preparation of these compounds in a combinatorial manner, is also disclosed.

3 Claims, 6 Drawing Sheets

COMBINATORIAL SYNTHESIS OF LIBRARIES OF MACROCYCLIC COMPOUNDS USEFUL IN DRUG DISCOVERY

RELATED APPLICATION DATA

The present application is a continuation application of U.S. patent application Ser. No. 13/218,784, filed Aug. 26, 2011, now allowed, which is a continuation application of U.S. patent application Ser. No. 11/615,332, filed Dec. 22, 2006, now U.S. Pat. No. 8,008,440, which is a continuation application of U.S. patent application Ser. No. 09/679,331, filed Oct. 4, 2000, now U.S. Pat. No. 7,169,899, which claims priority to Canadian Application No. 2,284,459, filed Oct. 4, 1999. The disclosures of each of which are incorporated by reference herein in their entireties.

FIELD OF THE INVENTION

The present invention relates to new macrocyclic compounds of biologically interesting structures. The invention also relates to a process for preparing these new compounds by lactam or Mitsunobu cyclization.

BACKGROUND OF THE INVENTION

As everybody knows, medicinal chemistry research has been dramatically transformed by biotechnology. Previously synthetic chemistry and natural products screening dominated drug research, but now molecular biology has become a driving force behind screening and the establishment of molecular targets.

Over the last years, most of the research in biotech companies has been directed to peptide and protein therapeutics in spite of problems associated with their low bioavailability, rapid metabolism, and lack of oral activity. Because of these limitations, research groups continue to rely upon chemical synthesis of nonpeptide substances for drug discovery, recognizing that small molecules are likely to remain the most viable avenue for the identification and optimization of potential drugs.

As is also known, combinatorial chemistry is a technique by which large chemical libraries can be generated by connecting together appropriate chemical building blocks in a systematic way. The ability to generate such large, chemically diverse libraries, either in a combinatiorial fashion or by any other high throughput parallel synthetic methods, combined with high throughput screening techniques, provides an immensely powerful tool for drug lead discovery and optimization.

Drug companies are increasingly interested in harnessing the ability of combinatorial synthesis to produce large collections (or libraries) of molecules to augment their existing sources of molecular diversity, and to fully exploit their capacity to capture millions of biological assay data points annually using high throughput robotic screening instrumentation.

This new science is still in its infancy, and to date most successful scaffold are derived from small heterocycles which are usually synthesized in very few steps. Thus several focused libraries have been built around bioactive cores such as benzodiazepines. However, this approach cannot be considered as a true method to generate innovative lead structures. Rather, it is a mean to optimize existing leads and is usually applied in drug development schemes.

Random libraries destined to search for innovative leads are very few today. As one example, a library based on diketopiperazine yielded a new submicromolar lead for a neurokinin-2 receptor after screening of this library on a variety of targets.

It is obvious that not all scaffolds may lead to potent drug candidates. Some very simple molecules requiring only one or two chemical steps may seem very attractive due to the huge size of the libraries that can be generated from them. Nonetheless, too simple molecules do not usually provide useful leads since they tend to lack target specificity, a prerequisite for a molecule to become a drug.

A class of organic structures with outstanding pharmaceutical activity has been termed as "macrocycle family". Compounds like Taxol, Epothilone, Erythromycin, Neocarzinostatin, Rifampin and Amphotericin are either under clinical study or already marketed drugs and belong to this important family. Most of these products are of natural origin, since they are not usually tackled by medicinal chemists due to lack of knowledge associated with their synthesis.

Over the last years, the present inventors have developed expertise in the field of macrocycles synthesis. With such an expertise, they have developed a method of synthesis and evaluation of libraries of partially peptidic macrocycles which mimic β-turns, thereby making it possible to quickly explore huge quantities of conformationally restricted structures.

OBJECTS AND SUMMARY OF THE INVENTION

A first object of the present invention is to provide a process for preparing macrocyclic compounds, which process can be carried out with a large variety of functional groups and in the presence of a large variety of solvent systems and resins, and thus can be used for preparing a large variety of macrocyclic compounds of biologically interesting structures that could be used for carrying out screening assays or as instrumental for the synthesis of other macrocyclic compounds. Libraries of such synthetic compounds should actually be as attractive as the libraries of extracted natural products which are presently used in high throughput biological screening assays.

Another object of the invention is to provide libraries of macrocyclic compounds incorporating two to five building units: one to four amino-acids and a tether chain for controlling the overall shape of the molecule.

More specifically, the macrocyclic compounds of the invention have the general formula (I):

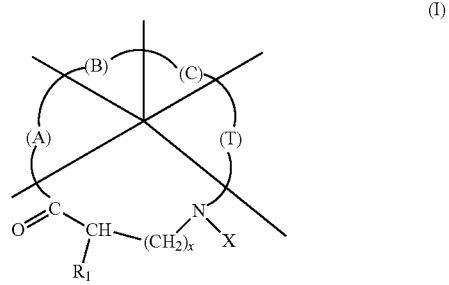

where part (A) is a

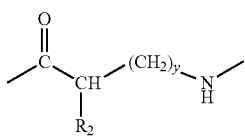

bivalent radical having its —NH— group linked to the carbonyl group of part

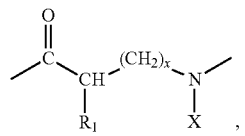

a —(CH$_2$)$_y$— bivalent radical, or a covalent bond;
where part (B) is a

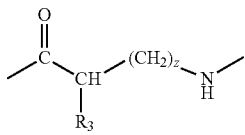

bivalent radical having its —NH— group linked to part (A), a —(CH$_2$)$_z$— bivalent radical, or a covalent bond;
where part (C) is a

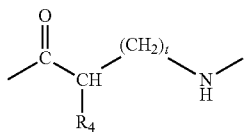

bivalent radical having its —NH— group linked to part (B), a —(CH$_2$)$_t$— bivalent radical, or a covalent bond;
where part (T) is a —Y-L-Z— radical; and
where X is a monovalent group selected from the group consisting of: —SO$_2$—Ar, —SO$_2$—CH$_3$, —SO$_2$—CF$_3$, —H, —COH, —CO—CH3, —CO—Ar, —CO—R, —CO—NHR, —CO—NHAr, —CO—O-tBu, —CO—O—CH$_2$—Ar

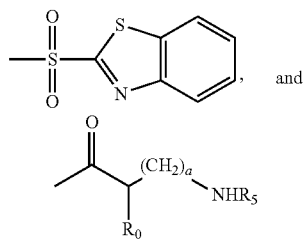

Ar being an aromatic group or substituted aromatic group,
a being an integer selected from the group consisting of 0, 1 and 2,
R being a monovalent group —(CH$_2$)$_n$—CH$_3$ or —(CH$_2$)$_n$—Ar with n being an integer from 1 to 16, $R_0$, $R_1$, $R_2$, $R_3$ and $R_4$ being independently selected from the group consisting of:

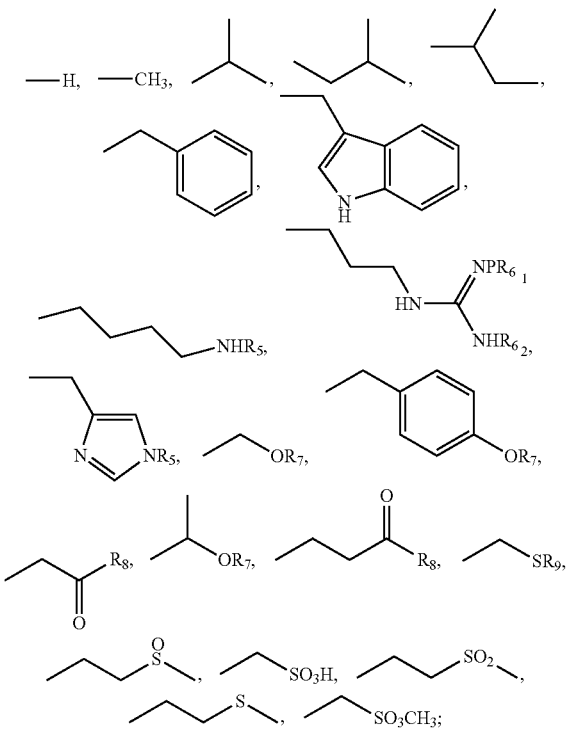

$R_5$, $R_{6_1}$ and $R_{6_2}$ each being a monovalent radical independently selected from the group consisting of: —H, —SO$_2$—CH$_3$, —SO$_2$—CF$_3$, —COH, —COCH$_3$, —CO—Ar, —CO—R or —CO—NHR wherein R is defined as above, —CONHAr, —COO-tBu and —COO—CH2-Ar, said radical being or not substituted by at least one monovalent group selected in the group consisting of:
—O—CH$_3$, —CH$_3$, —NO$_2$, —NH$_2$, —NH—CH$_3$, —N(CH$_3$)$_2$, —CO—OH, —CO—O—CH$_3$, —CO—CH$_3$, —CO—NH$_2$, OH, F, Cl, Br and I;

$R_7$ being a monovalent radical selected from the group consisting of:
—H, —COH, —CO—CH$_3$, —CO—R wherein R is defined as above, —CO—Ar and —CO-tBu, said radical being substituted or not by at least one substituent selected from the group consisting of:
—O—CH$_3$, —CH$_3$, —NO$_2$, —NH$_2$, —NH—CH$_3$, —N(CH$_3$)$_2$, —CO—OH, —CO—O—CH$_3$, —CO—CH$_3$, —CO—NH$_2$, OH, F, Cl, Br and I;

$R_8$ being a monovalent radical selected from the group consisting of: —OH, —NH$_2$, —OCH$_3$, —NHCH$_3$, —O-tBu and —O—CH$_2$—Ar, said radical substituted or not by at least one group selected in the group consisting of:
—O—CH$_3$, —CH$_3$, —NO$_2$, —NH—CH$_3$, —N(CH$_3$)$_2$, —CO—OH, —CO—O—CH$_3$, —CO—CH$_3$, —CO—NH$_2$, OH, F, Cl, Br, and I;

$R_9$ being a monovalent radical selected in the group consisting of: —H, -tBu, —CO—CH$_3$, —COAr, —CO—R wherein R is defined as above and —COH, said radicals substituted or not by at least one monovalent group selected from the group consisting of:

—O—CH$_3$, —CH$_3$, —NO$_2$, —NH—CH$_3$, —N(CH$_3$)$_2$, —CO—OH, —CO—O—CH$_3$, —CO—CH$_3$, —CO—NH$_2$, OH, F, Cl, Br and, I;

where Y is a bivalent group —CH$_2$— or —CO—;
where Z is a bivalent group —NH— or —O—;
wherein x, y, z and t are integers each independently selected from the group consisting of 0, 1 and 2;
wherein L is a bivalent radical selected from the group consisting of:

—(CH$_2$)$_d$-A-(CH$_2$)$_j$—B—(CH$_2$)$_e$—, d and e being independently an integer from 1 to 5, j being an integer from 0 to 5, with A and B being independently selected from the group consisting of:
—O—, —NH—, —NR— wherein R is defined as above, —S—, —CO—, —SO—, —CO—O—, —O—CO—, —CO—NH—, —NH—CO—, —SO$_2$—NH—, —NH—SO$_2$—,

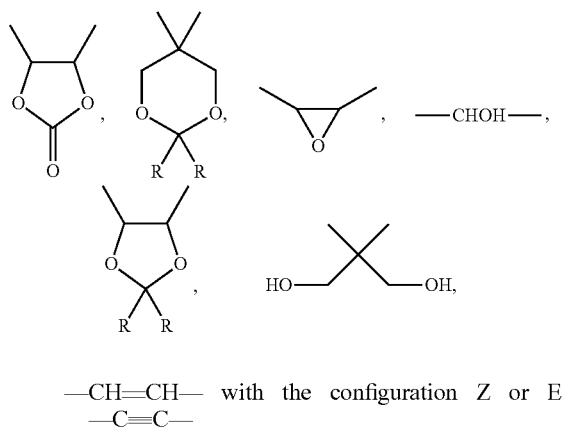

—CH═CH— with the configuration Z or E,
—C≡C— with the substituent -G$_2$- in a 1,2, 1,3 or 1,4 position,
G$_1$ being selected from the group consisting of:
—O—, —NH—, —NR— wherein R is defined as above, —S—, —CH═CH— with a Z configuration, and —CH═N—; and
G$_2$ being selected from the group consisting of:
—O—, —NH—, —CO—, —NR— wherein R is defined as above, —CO—O—, —O—CO—, —CO—NH—, —NH—CO—, —SO$_2$—NH— and —NH—SO$_2$—.

Salts of said compounds are also within the scope of the invention.

As may be understood, the new macrocyclic compounds according to the invention incorporate two to five building units, one to four amino-acids units and a tether chain which controls the shape of the molecule.

These compounds display enhanced stability towards peptidases and exhibit facilitated cell penetration as compared to the corresponding open chain linear equivalents.

Some of the compounds according to the invention include a β-turn motif within their rings:

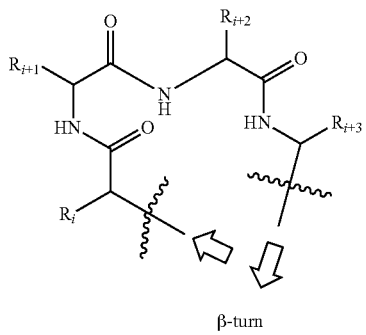

β-turn

It is known that β-turn is one of the three major motifs of peptide and protein secondary structure. β-turn plays a key role in many biological molecular recognition events including interactions between antigens and antibodies, peptide hormones and their receptors, and regulatory enzymes and their corresponding substrates. In order to attain high affinity and selective binding to a targeted receptor, a β-turn mimetic must reproduce both the functionality and the orientation of the side chains of the receptor-bound peptide ligand.

The inherent diversity in β-turn structure compounded with difficulties in identifying the key residues responsible for binding, make the design of β-turn mimetics quite challenging.

As may be appreciated, the present invention permits to circumvent the aforementioned difficulties by providing compounds which, thanks to their structure which incorporate numerous side chain combinations as well as multiple different side chain orientations, can be used as β-turn mimetics and evaluated accordingly.

Obviously, the preparation of libraries of β-turn mimetics represents a goal of the present invention. However, the latter is not exclusively restricted to such compounds. There are numerous other compounds according to the invention which include other interesting di- or tri-peptide motif with their structure whose active conformation need be probed by our conformation restrictive approach.

As is known many adhesive proteins present in extracellular matrices and in the blood contain the tripeptide arginine-glycine-aspartic acid (RTGD) as their cell recognition site. These proteins include fibronectin, vitronectin, osteopontin, callagens, thrombospondin, fibrinogen and von Willebrand factor. The RGD sequence of each of the adhesive proteins is recognized by at least one member of a family of structurally related receptors, integrins, which are heterodimeric proteins with two membrane-spanning sub-units. Some of these receptors bind to the RGD sequence of a single adhesion protein only, whereas others recognize groups of them. The conformation of the RGD sequence in the individual proteins may be critical to this recognition specificity. On the cytoplasmic side of the plasma membrane the receptors connect the extracellular matrix to the cytoskeleton.

More than ten proved or suspected RGD-containing adhesion-promoting proteins have already been identified, and the integrin family includes at least as many receptors recognizing these proteins. Together the adhesion proteins and their receptors constitute a versatile recognition system providing cells with anchorage, traction for migration, and signals for polarity, position, differentiation and possibly growth. Compounds according to the invention containing the sequence Arg-Gly-Asp in a controlled topology could inhibit cell to cell adhesion processes. Such compounds could be important in the areas of antithrombotic and cancer research.

Also included within the scope of the invention are compounds of the above mentioned formula (I) containing a biaryl bridge.

As can be appreciated, the compounds according to the invention have much flexibility and can adopt structures very different from conventional β-turns, according to the nature of their spacer parts. This means that the scope of the invention is broad and molecular modeling design allows the design of β and non-β-turns.

A main advantage of the invention is that the compounds of the formula (I) are neither too tight like small rings nor too loose like aliphatic chains.

The process according to the invention for preparing the above mentioned compounds basically comprises the following steps:

a) preparing by coupling a first building block deriving from natural or synthetic amino-acids, said first building block being of the formula:

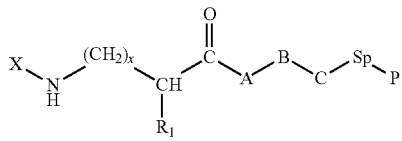

wherein X, R₁, A, B, C are defined as hereinabove, Sp is

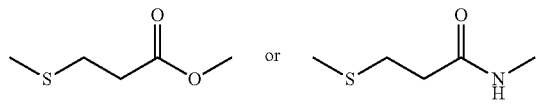

and P is —CH₃ or —CH₂-Ph where the coupling is carried out in liquid phase and Sp is

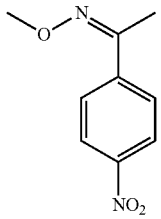

and P is polystyrene when the coupling is carried out in solid phase;

b) coupling the first building block prepared in step a) with a second building block hereafter called "tether", of the formula:

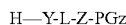

H—Y-L-Z-PGz wherein Y, L and Z are defined as and PGz is a protective group; and c) removing the protection groups PGz from the compound obtained in step b); and d) carrying out a macrocyclization of the unprotected product obtained in step c) and a cleavage if the preparing and coupling steps (a), (b) were carried out in the solid phase in order to obtain the requested compound of the formula (I).

As can be noted, this process uses lactam or Mitsunob cyclization to prepare the libraries of compounds according to the invention. It is very versatile and can be carried out in a combinatorial manner, either in solid phase or in solution phase.

The invention and its advantages will be better understood upon reading the following non restrictive detailed description and examples made with reference to the accompanying drawings.

DETAILED DESCRIPTION OF THE INVENTION

Figure 1:
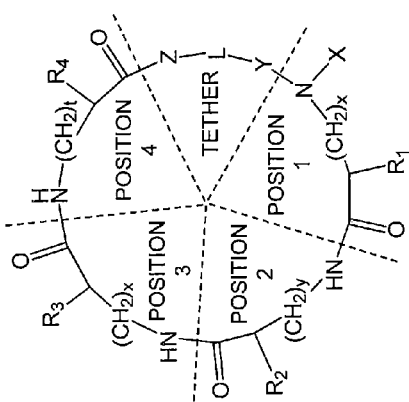
FIG. 1 is a table detailing the structure that may have the compounds of the formula (I) according to the invention.

As aforesaid, the process according to the invention is versatile enough to prepare a large number macrocyclic compounds, the main "families" of which are illustrated in FIG. 1. This process comprises the following basic steps:

a) preparing by coupling a first building block deriving from natural or synthetic amino-acids, b) coupling the first building block prepared in step a) with a second building block called "tether", c) removing the protective group from the compound obtained in step b), and d) carrying out a macrocyclization of the unprotected product obtained in step c) to obtain the requested compound.

As aforesaid, the process permits to prepare a large number of compounds either in a solution phase or on a solid support using an IRORI combinatorial chemistry set up or another set up like an Argonaut apparatus.

Figure 2A:
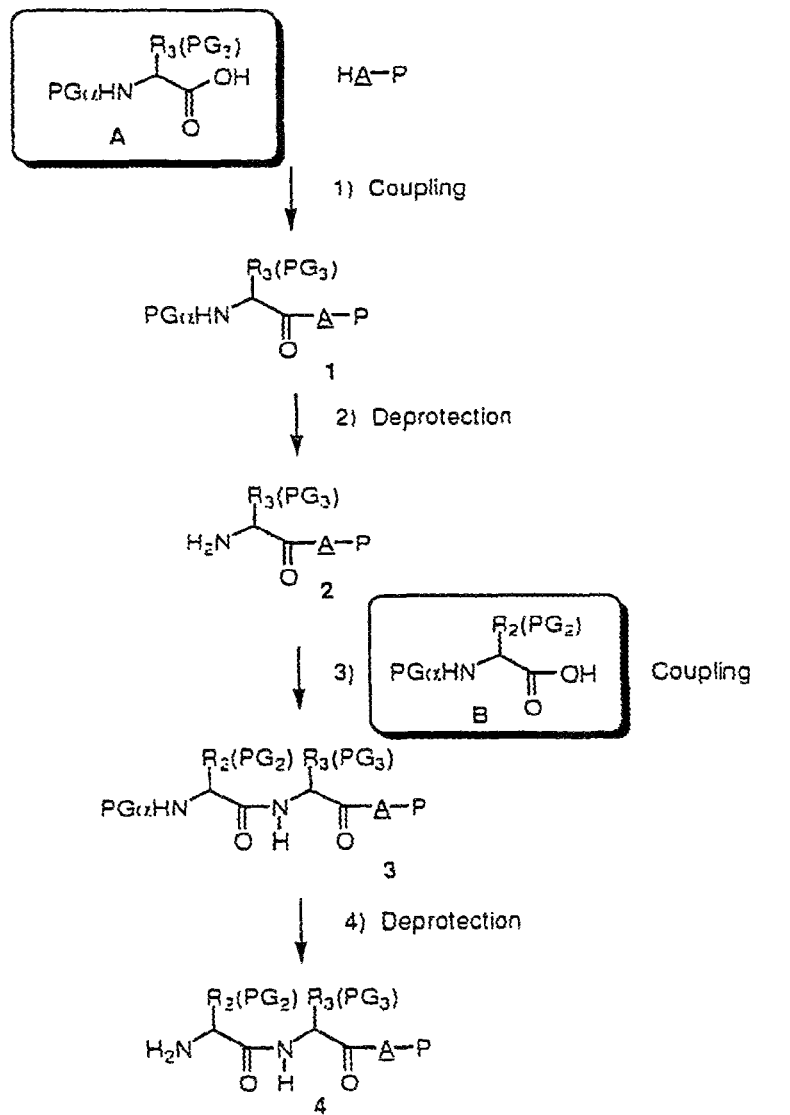
FIGS. 2a and 2b are schematic illustrations of the sequence of steps that must be carried out to obtain the library of compounds of formula (8), which is part of the "family 2" libraries shown in FIG. 1 for which Y is a methylene group (—CH₂—), and the amino-acids at positions 1, 2 and 3 are α-amino-acids (x, y, z=0).

In the synthesis shown in FIG. 2a, a first suitably protected amino-acid identified as "A" is activated as a thioester (solution phase or solid phase) or as an oxime ester (Kaiser resin solid phase support) to give a compound of formula (1). The amine protection (PGα in the case of α-amino-acids PGβ in the case of β-amino-acids and PGγ in the case of γ-amino-acids) is removed to give the compound of formula (2). A second amino-acid identified as "B" is then added in the same way to give a compound of formula (3), followed again by removal of the amine protection to give a compound of formula (4). A third acid of formula (C) (FIG. 2b) is coupled to the amine of formula (4) to yield a sulfonamide of the formula (5), which is immediately coupled with an alcohol of the formula (D) under Mitsunobu conditions to give a compound of formula (6). This compound of formula (6) can also be obtained directly from the compound of formula (4) by peptide coupling with an acid of formula (E). The terminal alcohol (Z═O) or amine (Z═NH) protecting group (PGz) is then cleaved to give the corresponding alcohol or amine of formula (7), which can undergo cyclization and cleavage all at once to give requested compound according to the invention of formula (8).

Figure 3:
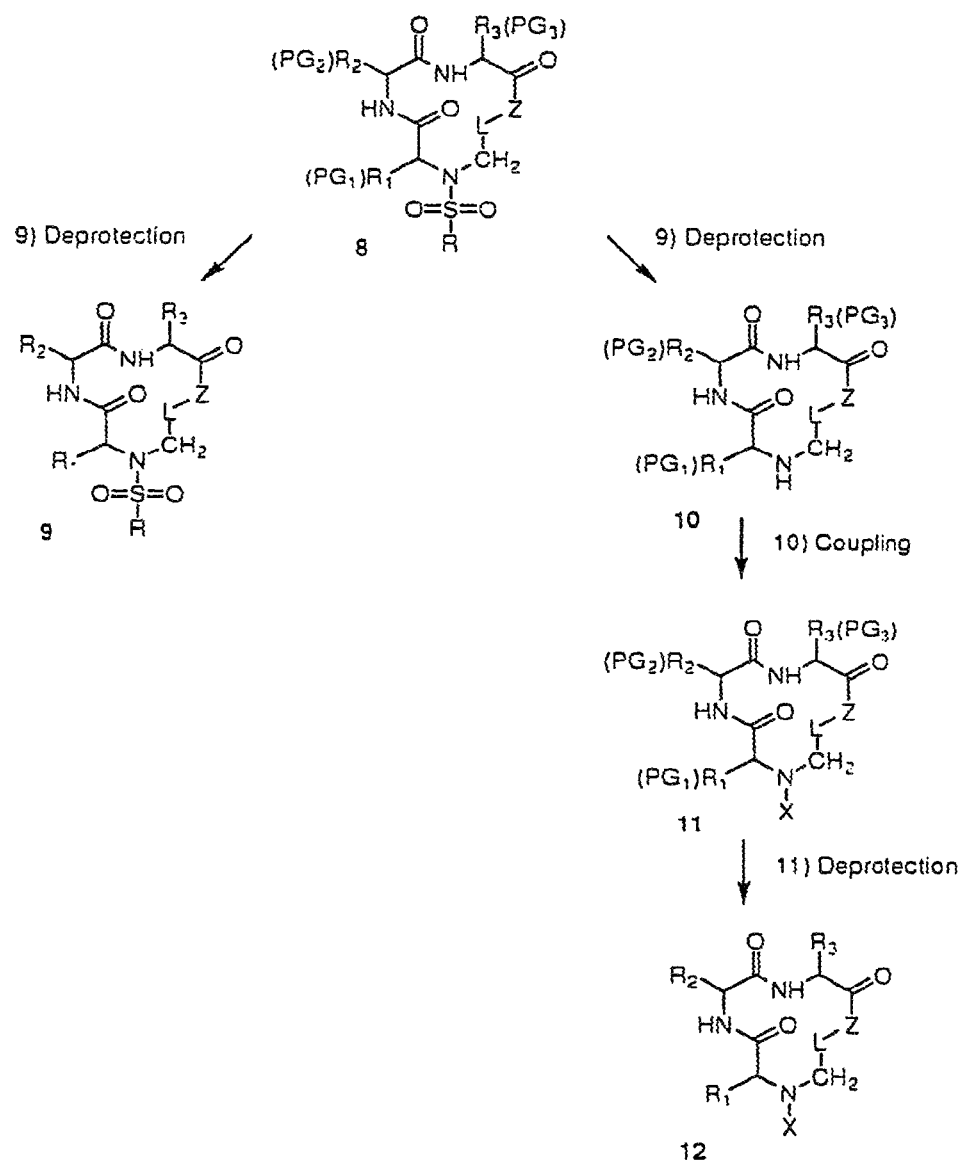
FIG. 3 is a schematic illustration of the steps that must be carried out to obtain other libraries of compounds of formulae (9) to (12), which are also parts of the "family 2" libraries shown in FIG. 1, for which Y is a methylene group (—CH₂—), and the amino-acids at positions 1, 2 and 3 are α-amino-acids (x, y, z=0).

As shown in FIG. 3, the orthogonal protections (PG1, PG2, PG3 and PG4 when a fourth amino-acid is introduced) of the compound of formula (8) can be removed to yield the compound according to the invention of formula (9). Another compound according to the invention of formula (10) can be obtained from the compound of formula (8) by cleaving the sulfonamide portion of the molecules. The resulting free amine can be coupled with various acids (see X groups in FIG. 1) to yield a compound of formula (11) according to the invention. Subsequent cleavage of the orthogonal protecting groups (PG0 when X is an amino-acid, PG1, PG2, PG3 and PG4 when a fourth amino-acid is introduced) yields a compound of formula (12) according to the invention.

Figure 4A:
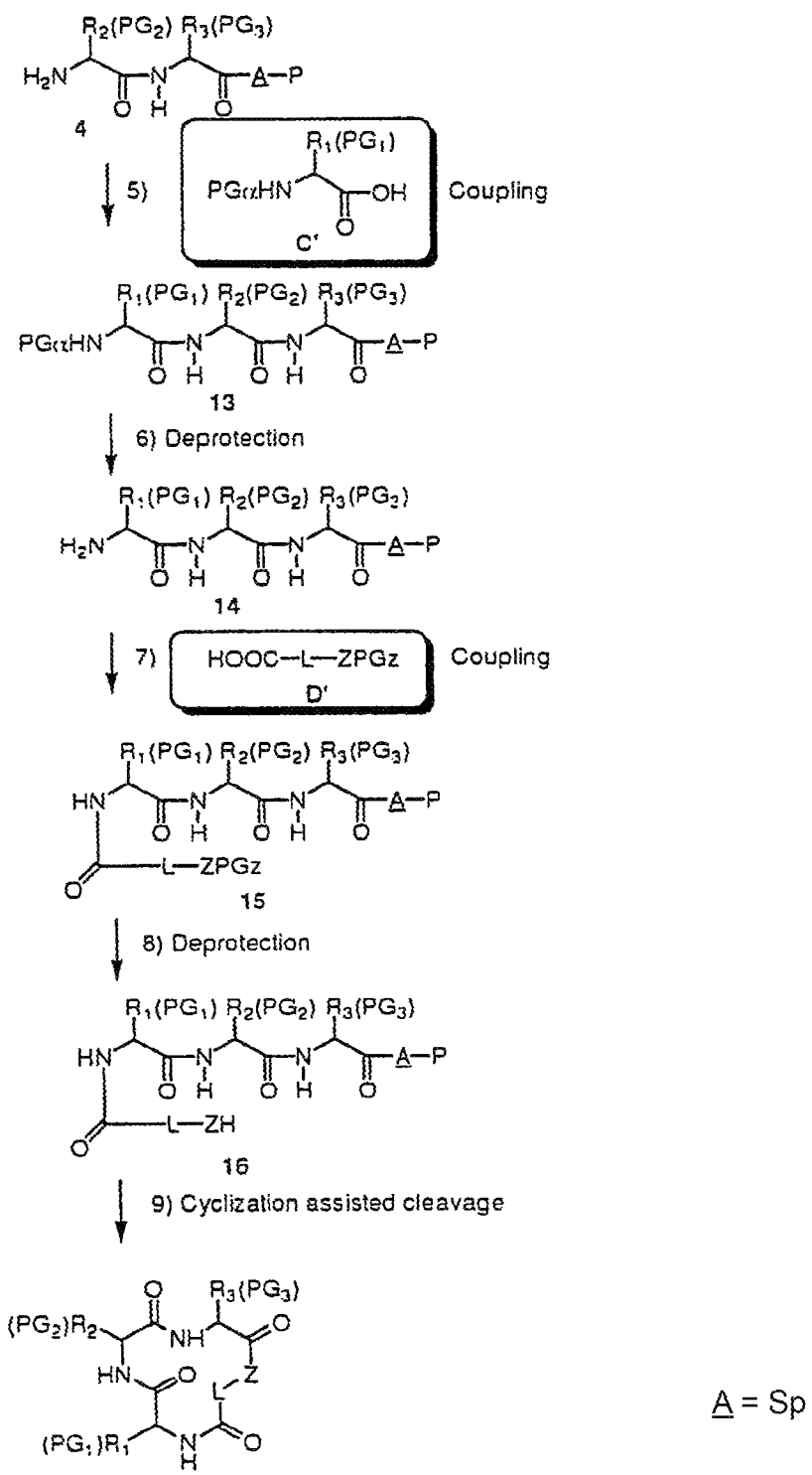
FIGS. 4a and 4b are schematic illustrations of the sequence of steps that must be carried out to obtain libraries of compounds of the formulae (17) and (18) which are parts of the "family 2" libraries shown in FIG. 1, for which Y is a carbonyl group (CO), and the amino-acids at positions 1, 2 and 3 are α-amino-acids (x, y, z=0).
Figure 4B:
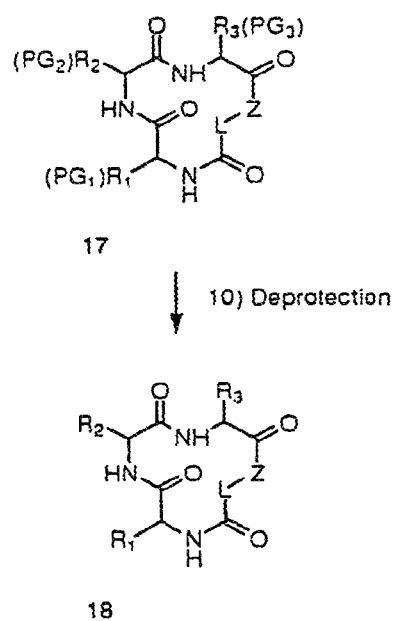

As shown in FIG. 4, it is also possible from the amine of formula (4) to couple an amino-acid of formula (C') to yield a compound of formula (13) according to the invention, whose amine protecting group (PGα, PGβ or PGγ) can be cleaved to give the amine of formula (14). A hydroxy-acid (Z=O) or amino-acid (Z=NH) of formula (D') is then coupled to yield a compound according to the invention of formula (15). The terminal alcohol (Z=0) or amine (Z=NH) protecting group (PGz) is then cleaved to give the corresponding alcohol or amine of formula (16), which can undergo cyclization and cleavage all at once to yield a compound according to the invention of formula (17). The orthogonal protections (PG1, PG2, PG3 and PG4 when a fourth amino-acid is introduced) of the compound of formula (17) see FIG. 4b can be removed to yield a compound of formula (18).

The above example of synthesis deals with the preparation of libraries of the "family 2" type for which positions 1, 2 and 3 are filled. Libraries of "families 1, 3 and 4" type as shown in FIG. 1 can be prepared exactly in the same way. In "family 1" type libraries, an extra amino-acid is incorporated at position 4. In "family 3" type libraries, positions 3 and 4 are empty and in "family 4" type libraries positions 2, 3 and 4 are empty.

Thus, it is possible to develop chemical libraries of dozens, hundreds, and even many thousands of discrete chemical compounds, in an efficient and reliable manner. This being the case, it is possible to use these libraries as chemical intermediates for the preparation of pharmaceutical compounds or for the identification of such pharmaceutical compounds or other useful species. Some of these compounds could also be used without further modification. Accordingly, the ability to prepare such complex libraries in a reliable and predictable fashion is highly desired.

The term "pharmaceutical" as used herein means the ability of the compounds to provide some therapeutic or physiological beneficial effect. As used herein, the term includes any physiologically or pharmacologically activity that produces a localized or systemic effect or effects in animals including warm blooded mammals such as humans. Pharmaceutically active agents may act on the peripheral nerves, adrenegic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, the autocoid system, the alimentary and excretory systems, the histamine system and central nervous systems as well as other biological systems. Thus, compounds derived from compositions of the present invention may be used as sedatives, psychic energizers, tranquilizers, anticonvulsant, muscle relaxants, anti-Parkinson agents, analgesics, anti-inflammatories, local anesthetics, muscle contractants, antibiotic, antiviral, antiretroviral, antimalarials, diuretics, lipid regulating agents, antiandrogenic agents, antiparasities, neoplastics and chemotherapy agents. These compounds could further be used to treat cardiovascular diseases, central nervous system diseases, cancer metabolic disorders, infections and dermatological diseases as well as other biological disorders and infections.

Among the potential uses of the compounds according the present invention are uses in scientific research as research reagents. In accordance with the present invention, it is now possible to prepare pluralities of compounds to create libraries of compounds for research. Such libraries are known to be useful and are important in the discovery of new drugs. In view of the chemical and conformational diversities of such compounds e.g. the large number of functionalizable sites, a very large number of different compounds can be prepared. Moreover, such compounds can be prepared differentially, that is, in such a fashion that a population of known species can be prepared reliably, ensuring that all potential members of a family of chemical species are in fact synthesized.

In view of the foregoing, persons of ordinary skill in the art will know how to synthesize such libraries, comprising chemical compositions within the scope and spirit of this invention and to assay the libraries against etiological agents or in tests or assays, in order to identify compounds having antibacterial, antifungal, antiviral, antineoplastic or other desired pharmaceutical, biological, or chemical activity.

SPECIFIC EXAMPLES

Preparation of macrocyclic compounds according to the invention by the process outlined above will be illustrated by the following non-limiting specific examples:

Example 1

Library of 135 members (solution phase)(see FIG. 2a)

This library (family 2 type) consists of a linear sequence of three natural L-α-amino-acids linked together by an aliphatic chain with 4 or 5 carbons in a head to tail manner. The first amino acids ($AA_1$) are glycine, leucine and methionine, the second ones ($AA_2$) are glycine, histidine (Doc), leucine, proline and valine, and the third ones ($AA_3$) are gylcine, methionine and phenylalanine.

The three third amino acids (Boc-AA3) were converted to their thioesters by coupling with methyl 3-mercapto-propionate. The formed compounds were coupled with the second five amino acids to produce 15 dipeptides which were then converted to 135 linear tripeptides by coupling with nine N-alkylated N-betsyl amino-acids. The end-to-end cyclization of the linear tripeptide thioesters was achieved by silver cation-assisted lactamization.

Amino Acid, Thioesters (Boc-$AA_3$-S($CH_2$)$_2CO_2$Me):

Chlorotrimethylsilane (276 mL, 2.18 mol) was added slowly to a solution of 3-mercaptopropionic acid (70 g, 0.66 mol) in methanol (267 mL, 6.6 mol) at −10° C. The reaction mixture was then stirred for 1 h at 0° C. and for 1 h at room temperature. The mixture was neutralized with saturated aqueous sodium bicarbonate to pH 8 and extracted with dichloromethane (3×300 mL). The combined organic phase was washed with saturated aqueous sodium bicarbonate (2×200 mL), brine (2×200 mL), dried over magnesium sulfate, filtered and evaporated under reduced pressure. The residue was then distilled (70° C./20 mmHg) to give methyl 3-mercaptopropionate as a colorless oil (61.2 g) in the yield of 77%.

1-(3-dimethylaminopropyl)-3-ethylcarbodiimide hydrochloride (42 mmol) was added to a solution of N-Boc amino-acid (33 mmol), methyl 3-mercaptopropionate (30 mmol) and 4-dimethylaminopyridine (3 mmol) in dichloromethane (80 mL) at 0° C. The resulting mixture was stirred for 1 hour at 0° C. and 30 min at room temperature. The reaction mixture was diluted with ethyl acetate (200 mL), washed with 1N hydrochloric acid (2×50 mL), saturated aqueous sodium bicarbonate (2×50 mL), brine (2×50 mL), dried over magnesium sulfate, and evaporated to give the desired thioester (Boc-$AA_3$-S($CH_2$)$_2$$CO_2$Me) in yields ranging from 95 to 100%.

Dipeptides (Boc-$AA_3$-S($CH_2$)$_2$$CO_2$Me):

To a solution of the N-Boc amino acid thioester (Boc-$AA_3$-S($CH_2$)$_2$$CO_2$Me) (5 mmol) in dichloromethane (2 mL), triethylsilane (10 mmol) was added, followed by trifluoro-acetic acid (3 mL). The reaction mixture was stirred for 1 h at room temperature, then diluted with toluene (2×10 mL) and the solvent was evaporated to give the TFA salt of H-$AA_3$-S($CH_2$)$_2$$CO_2$Me.

To a solution of N-Boc amino acid (Boc-$AA_2$-OH) (5 mmol) and 1-hydroxybenzotriazole (5 mmol) in tetrahydrofuran (5 mL) and dichloromethane (5 mL) at 0° C., 1-(3-dimethylamino-propyl)-3-ethylcarbodiimide hydrochloride (7 mmol) was added. The resulting mixture was stirred for 5 min at 0° C. and for 20 min at room temperature, then cooled down to 0° C.

A solution of the TFA salt of H-$AA_3$-S($CH_2$)$_2$$CO_2$Me (5 mmol) in dichloromethane (5 mL) was added to the above reaction mixture at 0° C., followed by diisopropylethylamine (7.5 mmol). The resulting reaction mixture was then stirred at the same temperature for 10 min. The ice-water bath was removed and the reaction was stirred for 2 to 4 h at room temperature. Finally, the reaction mixture was diluted with ethyl acetate (80 mL) and washed with 1N hydrochloric acid (2×15 mL), saturated aqueous sodium bicarbonate (2×15 mL), brine (2×20 mL), dried over magnesium sulfate, and evaporated to give the dipeptide (Boc-$AA_2$-$AA_3$-S($CH_2$)$_2$$CO_2$Me) in yields ranging from of 80 to 100%.

Alkylated Tripeptides (N-Bts-(N-alkylated)-$AA_1$-$AA_2$-$AA_3$-S($CH_2$)$_2$$CO_2$Me):

To a solution of N-Boc dipeptide (0.5 mmol) in dichloromethane (1 mL), triethylsilane (2 mmol) was added, followed by trifluoroacetic acid (1 mL). The reaction mixture was stirred for 1 h at room temperature and then diluted with toluene (2×5 mL) and evaporated to give the dipeptide TFA salt.

To a solution of alkylated N-Betsyl amino acid (0.5 mmol) and 1-hydroxybenzotriazole (0.5 mmol) in tetrahydrofuran (2 mL) and dichloromethane (2 mL) at 0° C., 1-(3-dimethyl-aminopropyl)-3-ethylcarbodiimide hydrochloride (0.7 mmol) was added. The resulting mixture was stirred for 5 min at 0° C. then for 30 min at room temperature, and cooled down to 0° C.

A solution of the dipeptide TFA salt (0.5 mmol) in dichloromethane (2 mL) was added to the above reaction mixture at 0° C., followed by diisopropylethylamine (0.8 mmol). The reaction mixture was then stirred for 10 min at the same temperature. The ice-water bath was removed and the reaction was stirred for 2 to 4 h at room temperature. The reaction mixture was diluted with ethyl acetate (50 mL) and washed with 1N hydrochloric acid (2×10 mL), saturated aqueous sodium bicarbonate (2×10 mL), brine (2×10 mL), dried over magnesium sulfate, and evaporated to give the alkylated tripeptides (Bts-(N-alkylated)-$AA_1$-$AA_2$-$AA_3$-S($CH_2$)$_2$$CO_2$Me) with yields ranging from 11 to 100%.

Preparation of Cyclotripeptides:

To a solution of the alkylated tripeptide (Bts-(N-alkylated)-$AA_1$-$AA_2$-$AA_3$-S($CH_2$)$_2$$CO_2$Me) (0.5 mmol) in dichloromethane (1 mL), triethylsilane (2 mmol) was added, followed by trifluoroacetic acid (1 mL). The reaction mixture was stirred for 1 h at room temperature and then diluted with toluene (2×5 mL) and the solvent was evaporated to give the TFA salt of alkylated tripeptide.

To a solution of the TFA salt of alkylated tripeptide (0.5 mmol) in ethyl acetate (250 mL), diisopropylethylamine (1.0 mmol) and silver trifluoroacetate (1.5 mmol) were added. The reaction mixture was stirred for 1 to 3 h at room temperature (Thin Layer Chromatography monitoring of the reaction). Brine (50 mL) and 1.0 M aqueous sodium thiosulfate (30 mL) was added and stirred for 60 min. The organic phase was washed with saturated EDTA aqueous solution (2×50 mL), 1N hydrochloric acid (50 mL), brine (2×50 mL), dried over magnesium sulfate and evaporated to give the crude product. The crude can be purified by flash column chromatography if necessary.

TABLE 1

Results for the cyclic peptides with the E-alkene linker.

| Name | MW | Quantity (mg) | Yield (%) | Purity Level (%) | Name | MW | Quantity (mg) | Yield (%) | Purity Level (%) |
|---|---|---|---|---|---|---|---|---|---|
| c-B-GGG-1 | 451 | 25 | 14 | 100 | c-B-MLG-1 | 581 | 200 | 93 | 91 |
| c-B-GGM-1 | 525 | 170 | 77 | 94 | c-B-MLM-1 | 655 | 162 | 61 | 99 |
| c-B-GGF-1 | 541 | 60 | 44 | 96 | c-B-MLF-1 | 671 | 150 | 89 | 97 |
| c-B-LGG-1 | 507 | 180 | 87 | 92 | c-B-GPG-1 | 491 | 26 | 21 | 85 |
| c-B-LGM-1 | 581 | 95 | 40 | 95 | c-B-GPM-1 | 565 | 121 | nd | 87 |
| c-B-LGF-1 | 597 | 93 | 83 | 93 | c-B-GPF-1 | 581 | 80 | 62 | 89 |
| c-B-MGG-1 | 525 | 80 | 35 | 96 | c-B-LPG-1 | 547 | 73 | 63 | 97 |
| c-B-MGM-1 | 599 | 66 | 28 | 94 | c-B-LPM-1 | 621 | 28 | 31 | 55 |
| c-B-MGM-1 | 599 | 31 | 10 | 77 | c-B-LPF-1 | 637 | 25 | 9 | 85 |
| c-B-MGF-1 | 615 | 82 | 27 | 97 | c-B-LPF-1 | 637 | 135 | 64 | 92 |
| c-B-MGF-1 | 615 | 25 | 6 | 69 | c-B-MPG-1 | 565 | 102 | 58 | 91 |
| c-B-GHG-1 | 673 | 107 | 53 | 91 | c-B-MPM-1 | 639 | 10 | 98 | 99 |
| c-B-GHM-1 | 747 | 97 | 59 | 98 | c-B-MPF-1 | 655 | 140 | 61 | 76 |
| c-B-GHF-1 | 763 | 177 | 68 | 91 | c-B-GVG-1 | 493 | 100 | 56 | 100 |
| c-B-LHG-1 | 729 | 82 | 61 | 85 | c-B-GVM-1 | 567 | 13 | 9 | 59 |
| c-B-LHM-1 | 803 | 133 | 65 | 80 | c-B-GVF-1 | 583 | 142 | 75 | 80 |
| c-B-LHF-1 | 819 | 162 | 74 | 97 | c-B-LVG-1 | 549 | 142 | 77 | 96 |
| c-B-MHG-1 | 747 | 177 | 63 | 97 | c-B-LVM-1 | 623 | 78 | 95 | 90 |
| c-B-MHM-1 | 821 | 160 | 44 | 90 | c-B-LVF-1 | 639 | 290 | 85 | 89 |

TABLE 1-continued

Results for the cyclic peptides with the E-alkene linker.

| Name | MW | Quantity (mg) | Yield (%) | Purity Level (%) | Name | MW | Quantity (mg) | Yield (%) | Purity Level (%) |
|---|---|---|---|---|---|---|---|---|---|
| c-B-MHF-1 | 837 | 201 | 51 | 91 | c-B-MVG-1 | 567 | 303 | 95 | 90 |
| c-B-GLG-1 | 507 | 229 | 90 | 97 | c-B-MVM-1 | 641 | 26 | 66 | 96 |
| c-B-GLM-1 | 581 | 146 | 68 | 99 | c-B-MVF-1 | 657 | 222 | 64 | 85 |
| c-B-GLF-1 | 597 | 130 | 81 | 80 | c-B-LLM-1 | 637 | 123 | 69 | 95 |
| c-B-LLG-1 | 563 | 152 | 88 | 92 | c-B-LLF-1 | 653 | 221 | 97 | 96 |

TABLE 2

Results for the cyclic peptides with the Z-alkene linker.

| Name | MW | Quantity (mg) | Yield (%) | Purity (%) | Name | MW | Quantity (mg) | Yield (%) | Purity (%) |
|---|---|---|---|---|---|---|---|---|---|
| c-B-GGG-2 | 437 | 2 | 1 | 89 | c-B-MLG-2 | 567 | 308 | 55 | 56 |
| c-B-GGM-2 | 511 | 250 | 77 | 86 | c-B-MLM-2 | 641 | 38 | 5 | 28 |
| c-B-GGF-2 | 527 | 46 | 46 | 96 | c-B-MLF-2 | 657 | 206 | 32 | 44 |
| c-B-LGG-2 | 493 | 142 | 76 | 99 | c-B-GPG-2 | 477 | 31 | 29 | 92 |
| c-B-LGM-2 | 567 | 112 | 23 | 55 | c-B-GPM-2 | 551 | 76 | nd | 82 |
| c-B-LGF-2 | 583 | 64 | 35 | 67 | c-B-GPF-2 | 567 | 55 | 42 | 92 |
| c-B-MGG-2 | 511 | 56 | 49 | 96 | c-B-LPG-2 | 533 | 0 | nd | |
| c-B-MGM-2 | 585 | 28 | 10 | 87 | c-B-LPM-2 | 607 | 34 | 54 | 49 |
| c-B-MGM-2 | 585 | 40 | 14 | 77 | c-B-LPF-2 | 623 | 19 | 8 | 96 |
| c-B-MGF-2 | 601 | 75 | 20 | 94 | c-B-MPG-2 | 551 | 46 | 22 | 78 |
| c-B-MGF-2 | 601 | 32 | 9 | 88 | c-B-MPM-2 | 625 | 5 | 1 | 59 |
| c-B-GHG-2 | 659 | 80 | 49 | 93 | c-B-MPF-2 | 641 | 44 | 11 | 49 |
| c-B-GHM-2 | 733 | 52 | 22 | 63 | c-B-GVG-2 | 479 | 61 | 23 | 85 |
| c-B-GHF-2 | 749 | 159 | 39 | 66 | c-B-GVM-2 | 553 | 59 | 80 | 93 |
| c-B-LHG-2 | 715 | 72 | 47 | 94 | c-B-GVF-2 | 569 | 191 | 86 | 76 |
| c-B-LHM-2 | 789 | 111 | 31 | 51 | c-B-LVG-2 | 535 | 92 | 36 | 89 |
| c-B-LHF-2 | 805 | 169 | 46 | 67 | c-B-LVM-2 | 609 | 60 | 57 | 93 |
| c-B-MHG-2 | 733 | 30 | 9 | 98 | c-B-LVF-2 | 625 | 152 | 36 | 87 |
| c-B-MHM-2 | 807 | 90 | 6 | 42 | c-B-MVG-2 | 553 | 112 | 30 | 82 |
| c-B-MHF-2 | 823 | 159 | 30 | 69 | c-B-MVM-2 | 627 | 6 | 7 | 48 |
| c-B-GLG-2 | 493 | 166 | 97 | 100 | c-B-MVF-2 | 643 | 0 | nd | |
| c-B-GLM-2 | 567 | 143 | 85 | 97 | c-B-LLM-2 | 623 | 85 | 26 | 61 |
| c-B-GLF-2 | 583 | 90 | 32 | 57 | c-B-LLF-2 | 639 | 193 | 43 | 77 |
| c-B-LLG-2 | 549 | 110 | 48 | 94 | | | | | |

TABLE 3

Results for the cyclic peptides with the alkyne linker.

| Name | MW | Quantity (mg) | Yield (%) | Purity (%) | Name | MW | Quantity (mg) | Yield (%) | Purity (%) |
|---|---|---|---|---|---|---|---|---|---|
| c-B-GGG-3 | 435 | 11 | 6 | 96 | c-B-LLG-3 | 547 | 124 | 46 | 83 |
| c-B-GGM-3 | 509 | 258 | 58 | 85 | c-B-LLG-3 | 547 | 61 | 11 | 41 |
| c-B-GGF-3 | 525 | 15 | 9 | 93 | c-B-LLM-3 | 621 | 148 | 62 | 81 |
| c-B-LGG-3 | 491 | 150 | 69 | 91 | c-B-LLF-3 | 637 | 196 | 55 | 82 |
| c-B-LGM-3 | 565 | 60 | 22 | 98 | c-B-MLG-3 | 565 | 167 | 24 | 40 |
| c-B-LGM-3 | 565 | 86 | 27 | 84 | c-B-MLM-3 | 639 | 27 | 9 | 76 |
| c-B-LGF-3 | 581 | 36 | 34 | 91 | c-B-MLF-3 | 655 | 100 | 22 | 65 |
| c-B-LGF-3 | 581 | 10 | 8 | 91 | c-B-GPG-3 | 475 | 37 | 46 | 99 |
| c-B-LGF-3 | 581 | 22 | 18 | 83 | c-B-GPM-3 | 549 | 15 | 16 | 50 |
| c-B-MGG-3 | 509 | 60 | 38 | 89 | c-B-GPF-3 | 565 | 45 | 83 | 99 |
| c-B-MGM-3 | 583 | 32 | 12 | 96 | c-B-LPG-3 | 531 | 0 | 1 | 58 |
| c-B-MGM-3 | 583 | 54 | 17 | 83 | c-B-LPM-3 | 605 | 54 | 29 | 38 |
| c-B-MGF-3 | 599 | 96 | 31 | 98 | c-B-LPF-3 | 621 | 26 | 10 | 91 |
| c-B-MGF-3 | 599 | 55 | 13 | 73 | c-B-MPG-3 | 549 | 23 | 15 | 98 |
| c-B-GHG-3 | 657 | 104 | 54 | 94 | c-B-MPM-3 | 623 | 10 | 41 | 41 |
| c-B-GHM-3 | 731 | 52 | 26 | 61 | c-B-MPF-3 | 639 | 5 | nd | |
| c-B-GHF-3 | 747 | 80 | 24 | 81 | c-B-GVG-3 | 477 | 39 | 19 | 79 |
| c-B-LHG-3 | 713 | 119 | 70 | 85 | c-B-GVM-3 | 551 | 33 | 34 | 66 |
| c-B-LHM-3 | 787 | 173 | 66 | 73 | c-B-GVF-3 | 567 | 36 | 6 | 28 |
| c-B-LHF-3 | 803 | 224 | 64 | 75 | c-B-LVG-3 | 533 | 158 | 64 | 82 |

TABLE 3-continued

Results for the cyclic peptides with the alkyne linker.

| Name | MW | Quantity (mg) | Yield (%) | Purity (%) | Name | MW | Quantity (mg) | Yield (%) | Purity (%) |
|---|---|---|---|---|---|---|---|---|---|
| c-B-MHG-3 | 731 | 107 | 29 | 93 | c-B-LVM-3 | 607 | 75 | 64 | 83 |
| c-B-MHM-3 | 805 | 97 | 13 | 78 | c-B-LVF-3 | 623 | 356 | 64 | 79 |
| c-B-MHF-3 | 821 | 163 | 38 | 83 | c-B-MVG-3 | 551 | 285 | 63 | 62 |
| c-B-GLG-3 | 491 | 63 | 38 | 100 | c-B-MVM-3 | 625 | 8 | 9 | 50 |
| c-B-GLM-3 | 565 | 53 | 15 | 51 | c-B-MVF-3 | 641 | 123 | 31 | 77 |
| c-B-GLF-3 | 581 | 20 | 7 | 44 | | | | | |

Spectral Data for Betsylated c-Met-Leu-Phe-Linker Compounds:

Trans-linker (c-B-MLF-1):
$^1$H NMR (CDCl$_3$, 300 MHz): 8.32 (1 H, br), 8.19 (1 H, dd, J=8.0 and 1.7 Hz), 8.01 (1 H, dd, J=8.5 and 1.7 Hz), 7.70-7.59 (2 H, m), 7.34-7.22 (5 H, m), 6.91 (1 H, br), 6.66 (1H, br), 5.70-5.60 (1 H, m), 5.21-5.16 (1 H, m), 4.64-4.59 (2 H, m), 3.92-3.85 (3 H, m), 3.35-3.20 (2 H, m), 3.30 (1 H, dd, J=14.0 and 4.7 Hz), 3.16 (1 H, dd, J=13.9 and 9.3 Hz), 2.47-2.32 (3 H, m), 2.09-2.04 (3 H, m), 1.97 (3 H, s), 1.73-1.44 (3 H, m), 0.86 (3 H, d, J=6.3 Hz), 0.81 (3 H, d, J=6.3 Hz).
LC-MS: m/e: 671 (M$^+$)

Cis-linker (c-B-MLF-2):
$^1$H NMR (CDCl$_3$, 300 MHz): 8.65 (1 H, J=5.9 Hz), 8.05 (1 H, dd, J=8.9 and 1.6 Hz), 8.00 (1 H, d, J=8.1 Hz), 7.66-7.57 (2 H, m), 7.33-7.22 (3 H, m), 7.16 (2 H, d, J=7.1 Hz), 6.71-6.68 (2 H, m), 5.72-5.56 (2 H, m), 5.01 (1 H, t, J=7.3 Hz), 4.54 (1 H, dt, J=8.7 and 4.9 Hz), 4.08-4.00 (2 H, m), 3.94 (1 H, dd, J=16.4 and 7.3 Hz), 3.67-3.56 (2 H, m), 3.23 (1 H, dd, J=14.1 and 4.8 Hz), 3.00 (1 H, dd, J=14.1 and 9.0 Hz), 2.67-2.47 (2 H, m), 2.36-2.11 (1 H, m), 2.09 (3 H, s), 2.07-1.99 (1 H, m), 1.92-1.82 (1 H, m), 1.61-1.52 (1 H, m), 1.49-1.41 (1 H, m), 0.93 (3 H, d, J=6.5 Hz), 0.87 (3 H, d, J=6.3 Hz).
LC-MS: m/e: 657 (M$^+$).

Acetylene-linker (c-B-MLF-3):
$^1$H NMR (CDCl$_3$, 300 MHz): 8.32 (2 H, d, J=8.1 Hz), 8.01 (1 H, d, J=8.0 Hz), 7.72-7.60 (2 H, m), 7.49 (1 H, br), 7.31-7.20 (5 H, m), 6.80 (1 H, br), 4.80-4.76 (1 H, m), 4.42-4.36 (2 H, m), 4.13-3.95 (3 H, m), 3.45-3.40 (1 H, m), 3.29 (1 H, dd, J=14.2 and 5.6 Hz), 3.14 (1 H, dd, J=14.1 and 10.1 Hz), 2.54-2.47 (3 H, m), 2.12-2.08 (1 H, m), 1.97 (3 H, s), 1.74 (2 H, t, J=7.6 Hz), 1.42-1.33 (1 H, m), 0.82 (3 H, d, J=6.6 Hz), 0.78 (3H, d, J=6.6 Hz).
LC-MS: m/e: 655 (M$^+$).

Example 2

Removal of Betsyl Group of Cyclotripeptides
1) In Solution:
Potassium trimethylsilanolate (0.2 mmol) was added to a solution of 2-naphthalenethiol (0.2 mmol) in a deoxygenated mixture of THF and EtOH (1:1, 1 mL) at room temperature and the resulting mixture was stirred for 20 min. N-Bts-cyclotripeptide (0.1 mmol) was then added. The resulting mixture was stirred for 1 h and evaporated to dryness. The residue was purified by column to give the deprotected product with yields ranging from 77 to 86%.
2) On Solid Support:
Polystyrene-thiophenol Resin (0.2 mmol) was added to a solution of potassium trimethylsilanolate (0.2 mmol) in a deoxygenated mixture of THF and EtOH (1:1, 1 mL) at room temperature and the resulting mixture stirred for 20 min. The solution was removed by filtration. The resin was washed with a deoxygenated mixture of THF and EtOH (1:1, 3×2 mL) and added to a solution of N-Bts-cyclotripeptide (0.1 mmol) in a deoxygenated mixture of THF and EtOH (1:1, 1 mL). The resulting mixture was stirred for 1 h. The resin was removed by filtration and washed with THF and EtOH (1:1 mixture, 2×2 mL). The filtrate was concentrated to give the crude product in quantitive yield.

Data for c-Met-Leu-Phe-Linker Compounds:
Trans-linker (c-MLF-1):
$^1$H NMR (CDCl$_3$, 300 MHz): 7.77 (1 H, d, J=7.7 Hz), 7.30-7.14 (5 H, m), 6.65 (1 H, d, J=7.4 Hz), 6.53 (1H, br), 5.56-5.64 (1 H, m), 5.32-5.22 (1 H, m), 4.03-3.95 (2 H, m), 3.79-3.68 (1 H, m), 3.57-3.35 (3 H, m), 3.12-3.02 (2 H, m), 2.96-2.86 (1 H, m), 2.61-2.50 (2H, m), 2.24-1.98 (3 H, m), 2.10 (3 H, s), 1.78 (2 H, m), 1.55-1.39 (2 H, m), 0.86 (3 H, d, J=6.6 Hz), 0.83 (3 H, d, J=6.8 Hz).
LC-MS: m/e: 474 (M$^+$)

Cis-linker (c-MLF-2):
$^1$H NMR (CDCl$_3$ & CD$_3$OD, 300 MHz): 7.27-7.14 (5 H, m), 5.80-5.71 (1 H, m), 5.68-5.53 (1 H, m), 4.21-4.09 (2 H, m), 3.88 (1 H, dd, J=14.0 and 6.0 Hz), 3.64 (1 H, dd, J=14.0 and 7.3 Hz), 3.34-3.15 (5 H, m), 2.52 (2 H, t, J=7.3 Hz), 2.07 (3 H, s), 2.00-1.86 (2 H, m), 1.53-1.15 (3 H, m), 0.80 (6H, d, J=6.6 Hz).
LC-MS: m/e: 460 (M$^+$).

Acetylene-linker (c-MLF-3):
$^1$H NMR (CDCl$_3$, 300 MHz): 7.92 (1 H, d, J=8.8 Hz), 7.34 (1 H, d, J=9.2 Hz), 7.31-7.17 (5 H, m), 7.02 (1 H, t, J=5.9 Hz), 4.21 (1 H, q, J=8.0 Hz), 4.10-3.99 (2 H, m), 3.79 (1 H, dm, J=15.5 Hz), 3.67 (1 H, dm, J=16.0 Hz), 3.49-3.35 (3 H, m), 3.25 (1 H, dd, J=8.8 and 4.3 Hz), 2.60-2.54 (2 H, m), 2.15-1.99 (1 H, m), 2.11 (3 H, s), 1.80-1.68 (2 H, m), 1.57-1.46 (2 H, m), 0.86 (6 H, d, J=6.3 Hz).
LC-MS: m/e: 458 (M$^+$).

Example 3

Preparation of N-Formyl-cyclotripeptides
The free amine macrocycle (see example 2) was added to a mixture of formic acid (0.2 mL) and acetic anhydride (0.1 mL) and the reaction mixture was stirred for 15 min at room temperature, then for 5 min at 55° C. and finally for 2 h at room temperature. The reaction mixture was evaporated to dryness and purified by column chromatography to give the desired compounds in yields ranging from 81 to 100%.

Data for Formylated c-Met-Leu-Phe-Linker Compounds:
Trans-linker (c-f-MLF-1):
$^1$H NMR (CDCl$_3$, 300 MHz): 8.72 (1 H, s), 7.92 (1 H, s), 7.38-7.22 (5 H, m), 6.78 (1H, br), 5.83 (1 H, d, J=10.0 Hz), 5.68-5.58 (1 H, m), 4.96-4.89 (1 H, m), 4.02-3.68 (5 H, m), 3.34 (1 H, dd, J=14.0 and 10.0 Hz), 2.78 (1 H, dd, J=13.5 and 5.2 Hz), 2.67-2.51 (3 H, m), 2.42-2.31 (1 H, m), 2.18-2.04 (1 H, m), 2.06 (3 H, s), 1.99-1.53 (6 H, m), 1.03 (3 H, d, J=6.0 Hz), 0.94 (3 H, d, J=6.0 Hz).
LC-MS: m/e: 502 (M$^+$) (84.2%).

Cis-Linker (c-f-MLF-2):
$^1$H NMR (CDCl$_3$, 300 MHz): 8.04 (1 H, s), 7.29-7.18 (5 H, m), 6.82-6.74 (1 H, m), 6.39 (1 H, d, J=9.5 Hz), 6.16 (1 H, dd, J=18.0 and 7.5 Hz), 6.94-6.85 (1 H, m), 4.80-4.72 (1 H, m), 4.24-3.68 (5 H, m), 3.50-3.43 (1 H, m), 2.87-2.79 (1 H, m), 2.61-2.45 (3 H, m), 2.14-2.01 (1 H, m), 2.11 (3 H, s), 1.74-1.62 (1 H, m), 1.43-1.25 (3 H, m), 0.93-0.78 (6 H, m).
LC-MS: m/e: 488 (M$^+$).

Acetylene-linker (c-f-MLF-3):
$^1$H NMR (CDCl$_3$, 300 MHz): 8.10 (1 H, s), 7.83 (1 H, br), 7.31-7.16 (5 H, m), 6.97 (1 H, br), 6.45 (1 H, br), 4.35-4.01 (5 H, m), 3.87-3.71 (2 H, m), 3.38 (1 H, dd, J=14.5 and 5.0 Hz), 3.24-3.16 (1 H, m), 2.59-2.23 (3 H, m), 2.08 (3 H, s), 1.66-1.25 (4 H, m), 0.84 (6H, t, J=6.0 Hz).
LC-MS: m/e: 486 (M$^+$).

Example 4

Solid Phase Synthesis on the Kaiser Resin
Anchoring Boc-amino Acid to the Resin:
To the Kaiser resin (2.0 g, 0.95 mmol/g) was added a 0.2M solution of N-Boc amino acid and 4-dimethylaminopyridine (0.25 eq). After shaking for 5 min, diisopropylcarbodiimide (1.5 eq) was added and the reaction mixture was agitated for 16 h. The resin was washed with dichloromethane (3×30 mL), tetrahydrofuran (1×30 mL), methanol (1×30 mL), dichloromethane (1×30 mL), methanol (1×20 mL), tetrahydrofuran (1×30 mL), methanol (1×20 mL), dichloromethane (2×30 mL) and dried by nitrogen flow. The unreacted hydroxy group on the resin was then capped by reacting with acetic anhydride (5 mL) and diisopropyl-ethylamine (1 mL) in dichloromethane (20 mL) at room temperature for 2 h. The resin was washed and dried by the same procedure mentioned above. The substitution level was 0.2-0.3 mmol/g.

Formation of Dipeptides (Performed on the Quest 210™):
25% TFA in dichloromethane (20 mL) was added to the above resin (0.4 mmol, 2.0 g, 0.2 mmol/g) and agitated for 30 min. The resin was then washed with dichloromethane (3×30 mL), methanol (1×20 mL), dichloromethane (1×30 mL), methanol (1×20 mL), dichloromethane (1×30 mL), methanol (1×20 mL), dichloromethane (2×30 mL) and dried by nitrogen flow.
A 0.2M solution of hydroxybenzotriazole and diisopropyl-carbodiimide in 60% dichloromethane/tetrahydrofuran was added to the N-Boc amino acid, followed by diisopropyl-ethylamine (1.5 eq). The resulting mixture was stirred for 30 min at room temperature, and then transferred to the resin (200 mg on Quest 210™) and agitated at room temperature for 30 min. Diisopropylethylamine (2.0 mmol) was then added and agitated until Kaiser test of an aliquot of the resin was negative (2 to 4 h). The resin was washed with dichloromethane (3×4 mL), tetrahydrofuran (1×4 mL), methanol (1×4 mL), dichloromethane (1×4 mL), methanol (1×4 mL), tetrahydrofuran (1×4 mL), methanol (1×4 mL), dichloromethane (2×4 mL) and dried by nitrogen flow.

Formation of Tripeptides:
25% TFA in dichloromethane (4 mL) was added to the Boc-protected dipeptide resin (0.04 mmol, 200 mg g, 0.2 mmol/g) and agitated for 30 min. The resin was then washed with dichloromethane (3×4 mL), methanol (1×4 mL), dichloro-methane (1×4 mL), methanol (1×4 mL), dichloromethane (1×4 mL), methanol (1×4 mL), dichloromethane (2×4 mL) and dried by nitrogen flow.
A 0.2M solution of hydroxybenzotriazole and diisopropyl-carbodiimide in 60% dichloromethane/tetrahydrofuran was added to the N-Bts amino acid, followed by diisopropyl-ethylamine (1.5 eq). The resulting mixture was stirred for 30 min at room temperature, and then transferred to the resin (200 mg on Quest 210™) and agitated at room temperature for 30 min. The resin was washed with dichloromethane (3×4 mL), tetrahydrofuran (1×4 mL), methanol (1×4 mL), dichloromethane (1×4 mL), methanol (1×4 mL), tetrahydrofuran (1×4 mL), methanol (1×4 mL), dichloromethane (2×4 mL) and dried by nitrogen flow.

Mitsunobu Reaction:
A 0.2M solution of 5-(tert-butoxycarbonylamino)-trans-2-penten-1-ol or N-tert-butoxycarbonyl-2-(2-hydroxyethoxy)-cinnamyl amine, and triphenylphosphine was added to the tripeptide resin (0.036 mmol, 180 mg, 0.2 mmol/g on the Quest 210™) in anhydrous tetrahydrofuran, followed by diethyl azodicarboxylated (1.5 eq). The mixture was agitated for 2 h and the resin was washed and dried by the same procedure mentioned above.

Cyclization of Alkylated Tripeptides:
The N-alkylated linear tripeptide (0.016 mmol, 80 mg) was treated with 25% TFA in dichloromethane (4 mL) for 30 min and washed with dichloromethane, methanol and dried by nitrogen flow.
Toluene (2 mL), acetic anhydride (1 mL) and diisopropyl-ethylamine (1 mL) were added to the above resin and agitated for 2 h. The resin was removed by filtration and washed with dichloromethane (3×4 mL). An aliquot of the filtrate was analysized by LC-MS. The filtrate was concentrated and then diluted with ethyl acetate (15 mL). The solution was washed with 1N hydrochloric acid (2 mL), saturated sodium bicarbonate (2 mL), brine (3 mL), dried and evaporated to give the crude product.

TABLE 4

Library of Macrocyclic Tripeptides Synthesized on the Kaiser Resin Using the Quest 210 ™:

| SAMPLE ID | ISOLATED QUANTITY (MG) | PURITY |
|---|---|---|
| c-B-MPG-1 | 5.9 (42%) | Low |
| c-B-MVG-1 | 4.4 (48%) | Medium |
| c-B-MGM-1 | 4.6 (32%) | Low |
| c-B-LPM-1 | 7.5 (50%) | Low |
| c-B-LLM-1 | 7.1 (46%) | Good |
| c-B-GVM-1 | 3.1 (22%) | Low |
| c-B-GLF-1 | 7.8 (81%) | Good |
| c-B-MVG-4* | 2.4 (23%) | Good |
| c-B-MGM-4* | 5.7 (34%) | Low |
| c-B-LPM-4* | 3.3 (19%) | Low |
| c-B-LMM-4* | 5.0 (29%) | Medium |
| c-B-GVM-4* | 4.0 (25%) | Low |
| c-B-GLF-4* | 2.9 (26%) | Low |

*Nature of linker 4 is shown in Scheme 2.

Example 5

Synthesis of Betsylated Macrocyclic Tripeptides on Thio-ester Resin in IRORI MACROKANS™:
Macrocyclic tripeptides were synthesized in MACRO-KANS™ (160 mg of aminomethyl resin) following the same procedure as that given for the synthesis on solid support (Kaiser Resin, see example 4):

TABLE 5

Library of Macrocyclic Tripeptides Synthesized

| SAMPLE ID | QUANTITY (MG) | PURITY |
|---|---|---|
| c-B-GHG-1 | 7.6 (6%) | Good |
| c-B-GLF-1 | 16.3 (14%) | Excellent |

TABLE 5-continued

Library of Macrocyclic Tripeptides Synthesized

| SAMPLE ID | QUANTITY (MG) | PURITY |
|---|---|---|
| c-B-GVM-1 | 20 (18%) | Good |
| c-B-LHF-1 | 43 (27%) | Excellent |
| c-B-LPM-1 | 26.7 (22%) | Excellent |
| c-B-LLM-1 | 20.6 (17%) | Excellent |
| c-B-MVG-1 | 10.5 (10%) | Good |
| c-B-MPG-1 | 6.4 (6%) | Low |
| c-B-GHG-4 | 12.4 (11%) | Excellent |
| c-B-GLF-4 | 12.4 (9%) | Excellent |
| c-B-GVM-4 | 9.3 (7%) | Good |
| c-B-LHF-4 | 21.8 (16%) | Excellent |
| c-B-LPM-4 | 29.1 (21%) | Excellent |
| c-B-LLM-4 | 25.8 (18%) | Excellent |
| c-B-MVG-4 | 37.5 (30%) | Excellent |
| c-B-MPG-4 | 30.3 (24%) | Excellent |

Example 6

Synthesis of Mesylated Macrocyclic Tripeptides on Thioester Resin in IRORI MINIKANS™

Macrocyclic tripeptides were synthesized in MINIKANS™ (60 mg of aminomethyl resin) following the same procedure as that given for the synthesison solid support (Kaiser Resin, see example 4):

TABLE 6

Library of Macrocyclic Tripeptides Synthesized

| SAMPLE ID | QUANTITY (MG) | PURITY |
|---|---|---|
| c-Ms-GLG-4 | 3 (9%) | Low |
| c-Ms-GLG-1 | 3 (12%) | Low |
| c-Ms-E(OMe)LG-4 | 1.9 (5%) | Good |
| c-Ms-E(Ome)LG-1 | 4 (13%) | Good |
| c-Ms-LPM-4 | 0.1 | Good |
| c-Ms-LPM-1 | 0.5 | Low |
| c-Ms-YLG-4 | 2 (5%) | Good |
| c-Ms-YLG-1 | 6 (18%) | Good |
| c-Ms-GLF-4 | 6 (16%) | Good |
| c-Ms-GLF-1 | 5 (15%) | Good |
| c-Ms-LLG-4 | 1 (3%) | Low |
| c-Ms-LLG-1 | — | Low |
| c-Ms-LLM-4 | — | Low |
| c-Ms-SLG-4 | — | Good |
| c-Ms-E(COOH)LG-4 | 13.3* | Good |
| c-Ms-E(COOH)LG-1 | 21* | Good |

*Unpurified

Specific Examples of Building Units

Tether Building Blocks (Type D, See FIG. 2b)
The tether building blocks have the following formula: HO—Y-L-Z-PGz.

The three following tether building blocks 4-(tert-butoxycarbonylamino)-cis-2-buten-1-ol (Y=$CH_2$, L=[Z]alkene, Z=$CH_2$) and 4-(tert-butoxycarbonylamino)-2-butyn-1-ol (Y=$CH_2$, L=alkyne, Z=$CH_2$) and 5-(tert-butoxycarbonylamino)-trans-2-penten-1-ol (Y=$CH_2$, L=$CH_2$-[E]alkene, Z=$CH_2$) were synthesized from commercial available cis-2-butene-1,4-diol, 2-butyne-1,4-diol and 3-amino-1-propanol respectively.

Preparation of 4-(tert-butoxycarbonylamino)-2-butyn-1-ol:

Dowex 50WX8-100 ion-exchange resin (53 g) was added to a suspension of 2-butyne-1,4-diol (153.9 g, 1.77 mol) and dihydropyran (250 mL, 2.66 mol) in dichloromethane (800 mL) at room temperature. The resulting mixture was stirred for 60 min and quenched with triethylamine (10 mL). The resin was removed by filtration. The filtrate was washed with a saturated aqueous solution of sodium bicarbonate (100 mL), brine (3×300 mL), dried over magnesium sulfate, filtered and evaporated under reduced pressure to give the desired monoprotected 2-butyne-1,4-diol with a yield of 50%.

To a solution of monoprotected 2-butyne-1,4-diol (20.4 g, 0.12 mol) and triphenylphosphine (40.9 g, 0.16 mol) in tetrahydrofuran (50 mL), hydrazoic acid (113 mL, 1.6 M in toluene, 0.18 mol) was added at 0° C. Diisopropyl azodicarboxylate (29.5 mL, 0.15 mol) was added dropwise to the solution whose temperature was around 0° C. The reaction was stirred for 30 min at 0° C. and for 30 min at room temperature. Triphenylphosphine (40.9 g, 0.16 mol) was added at 0° C. and the reaction was stirred overnight at room temperature. After addition of water (50 mL), the mixture was heated at 60° C. for 4 h, 1N hydrochloric acid (140 mL) was added. After stirring for 1 h, brine (140 mL) and dichloromethane (500 mL) were added. The aqueous phase was washed with dichloromethane (3×100 mL). Potassium carbonate (16.5 g, 0.12 mol) was added, followed by a solution of di-tert-butyl dicarbonate (26.2, 0.12 mol) in tetrahydrofuran (100 mL). The reaction mixture was stirred for 18 h, then extracted with dichloromethane (1×300 mL, 2×50 mL). The combined organic extract was washed with brine (50 mL), dried over magnesium sulfate, filtered and evaporated under reduced pressure. The residue was purified by a dry-pack silica gel column to give the titled compound in 50% yield.

Preparation of 4-(tert-butoxycarbonylamino)-cis-2-buten-1-ol:

The title compound was synthesized from cis-2-butene-1,4-diol in an overall yield of 30% according to the procedure used for 4-tert-butoxycarbonylamino-2-butyn-1-ol.

Preparation of 5-(tert-butoxycarbonylamino)-trans-2-penten-1-ol:

A solution of di-tert-butyl dicarbonate (382.8 g, 1.75 mol) in dichloromethane (1.6 L) was added to 3-amino-1-propanol (263.6 g, 3.51 mol) during 2 h. The reaction mixture was stirred for an additional 40 min and water (1 L) was added. The organic phase was washed with water (3×500 mL,), dried over magnesium sulfate, filtered and evaporated under reduced pressure to give 3-(tert-butoxycarbonylamino)-1-propanol in 96% yield.

Dimethyl sulfoxide (321 mL, 4.5 mol) and triethylamine (941 mL, 6.75 mol) were added to a solution of 3-tert-butoxycarbonylamino-1-propanol (262.6 g, 1.5 mol) in dichloromethane (1.2 L) at 0° C. Sulfur trioxide pyridine complex (286.4 g, 1.8 mol) was added in 6 portions. The reaction mixture was then stirred for 30 min at 0° C. and for 30 min at room temperature. The reaction was cooled down to 0° C., quenched with 1N hydrochloric acid, washed with brine (2×500 mL), dried over magnesium sulfate, filtered and evaporated under reduced pressure to give 3-(tert-butoxycarbonylamino)propionaldehyde.

To a solution of the above crude aldehyde (1.5 mol) in acetonitrile (1.3 L), trimethyl phosphonoacetate (409.7 g, 2.25 mol) and lithium hydroxide (53.9 g, 2.25 mol) were added and stirred overnight at room temperature. The reaction was quenched with water (50 mL).

The acetonitrile solvent was removed by evaporation under reduced pressure. The residue was then diluted with diethyl ether (800 mL), washed with 1N sodium hydroxide (3×300 mL), brine (2×500 mL), dried over magnesium sulfate, filtered and evaporated under reduced pressure to give the desired trans-unsaturated methyl ester.

Diisobutylaluminium hydride (1.12 L, 1.0 M in dichloromethane, 1.12 mol) was added dropwise to a solution of this methyl ester (102.75 g, 0.445 mol) in dichloromethane (250 mL) at 0° C. The resulting mixture was stirred for an additional 1 h and then poured slowly into a 1M tartaric acid aqueous solution (1.4 L), extracted with dichloro-methane (3×500 mL). The combined organic phase was dried over magnesium sulfate, filtered and evaporated under reduced pressure. The residue was purified by dry-pack silica gel column to give the titled compound with a yield of 40% for the three steps.

Amino-acid Building Block (Type A and B, See FIG. 2a)

The N-Boc amino acids are commercial available except $N^{\alpha}$-Boc-$N^{im}$-Doc-histidine which was prepared by the method described below.

Preparation of $N^{\alpha}$-Boc-$N^{im}$-Doc-histidine:

A solution of 2,4-dimethyl-3-pentanol (83.2 g, 0.72 mol) and triethylamine (125 mL, 0.90 mol) in toluene (300 mL) was added slowly (30 min) to a solution of phosgene (531 mL, 20% in toluene, 1.07 mol) in toluene (531 mL) at 0° C. The mixture was stirred for an additional 30 min at the same temperature. Ice-cold water (500 mL) was added and the organic phase was washed with ice-cold water (2×100 mL), dried over magnesium sulfate, filtered and evaporated under reduced pressure. The residue was then distilled under reduced pressure (6 cm of Hg, 33-35° C.) to give Doc-Cl as a colorless oil (92 g, 72%).

A solution of Doc-Cl (57.9 g, 0.32 mol) in tetrahydrofuran (250 mL) was added slowly to a solution $N^{\alpha}$-Boc-histidine (69 g, 0.27 mol) and potassium carbonate (41.1 g, 0.28 mol) in water (350 mL) at 0° C. The resulting mixture (pH=10) was stirred for 2 h at the same temperature and for 1 h at room temperature. Water (150 mL) and hexane (200 mL) were added to the reaction mixture. The separated aqueous phase was washed with a mixture of diethyl ether and hexane (1:1; 3×200 mL), acidified with 20% citric acid aqueous solution to pH 2-3, and then extracted with dichloromethane (3×200 mL). The combined dichloromethane solution was washed with brine (200 mL), dried over magnesium sulfate, filtered and evaporated under reduced pressure to give the crude 1\r-Boc-$N^{im}$-Doc-histidine in quantitive yield.

Figure 2B:
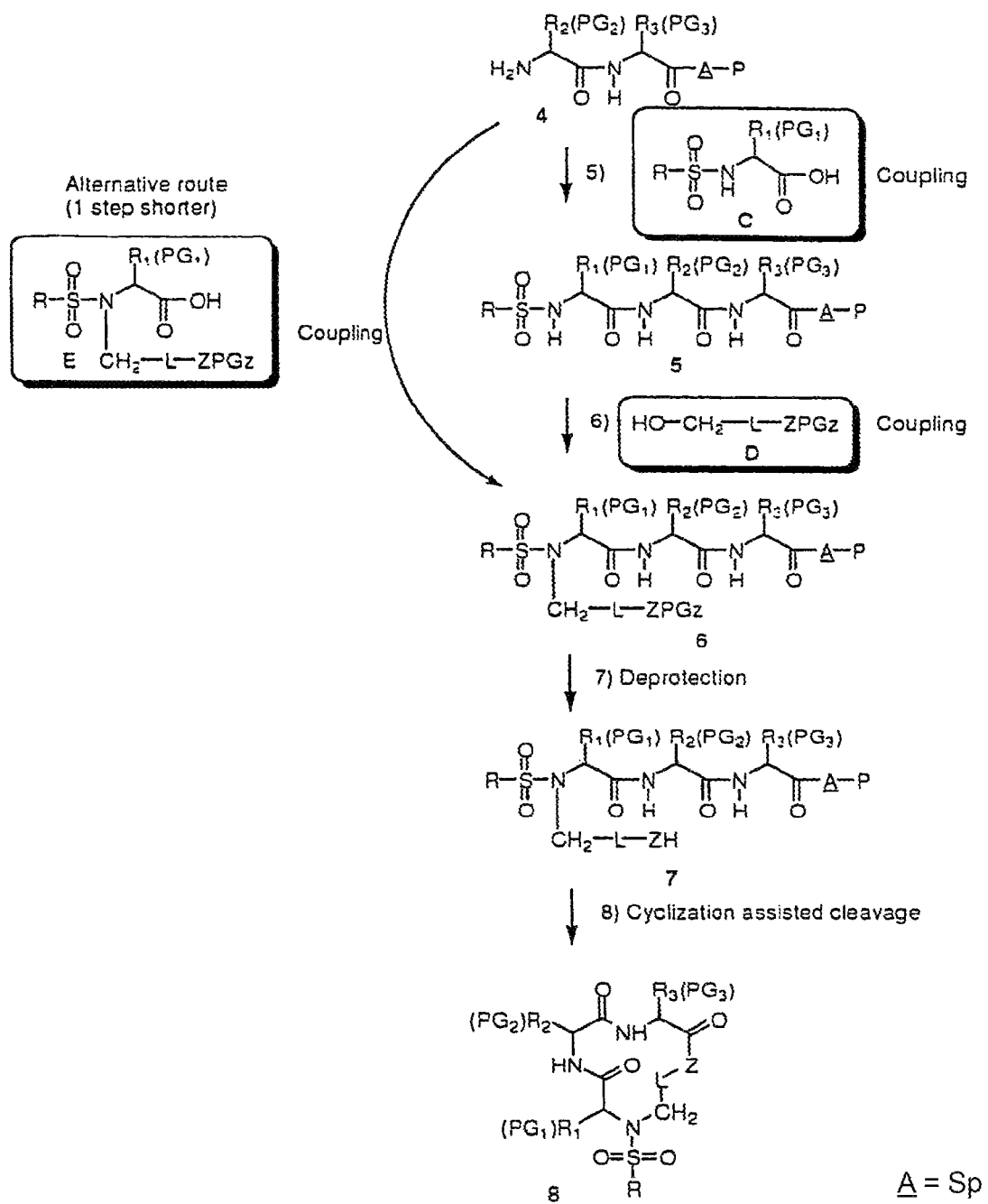

Building Blocks of Type C (See FIG. 2b)

N-Betsyl protected amino acids (Bts-AA1) were synthesized by the reaction of amino acids with Betsyl chloride (benzothiazole-2-sulfonylchloride) which was obtained from mercaptobenzothiazole and chlorine.

Preparation of N-Betsyl Amino Acid (Bts-$AA_1$OH):

Chloride gas was bubbled into a solution of acetic acid (250 mL) in water (500 mL) at 5° C. until an orange precipitate was formed in good quantity. A solution of mercaptobenzothiazole (0.7 mol) in aqueous acetic acid (750 mL, 33% in water) was added in portions to the above reaction mixture in a period of 3 hours. The reaction mixture was stirred for 1 h, filtered at 0° C. then washed with cold water. The solid was dissolved in cold dichloromethane (500 mL) and washed with cold brine (2×100 mL), cold saturated sodium bicarbonate (100 mL), brine (100 mL), dried over magnesium sulfate, filtered and evaporated at 10° C. under reduced pressure. The solid was then washed with cold diethyl ether (100 mL), cold acetonitrile (100 mL), filtered and pumped to give betsyl chloride (benzothiazole-2-sulfonylchloride).

To a solution of amino acid (0.11 mol) in 0.25 N aqueous sodium hydroxide (0.08 mol) at room temperature (initial pH around 9.5), betsyl chloride (0.1 mol) was added. The resulting mixture was stirred vigorously for 18 h. The pH of the reaction was adjusted between 9.5 to 10.0 with 1.0 N aqueous sodium hydroxide during the reaction progress. The reaction mixture was washed with diethyl ether (3×50 mL). The aqueous phase was then cooled to 0° C., acidified to pH 1.5-2.0 with 6 N HCl, and extracted with ethyl acetate (3×100 mL). The combined ethyl acetate solution was dried over magnesium sulfate, filtered and evaporated under reduced pressure to give the desired compound in 74-85% yield.

Building Blocks of Type E (See FIG. 2b)

These building blocks correspond to building blocks of type C which have been alkylated using Mitsunobu reaction conditions with the building blocks of type D. To be able to carry out this alkylation, the acid functional group of C must be protected. The protecting group used is finally removed to get the desired compounds Preparation of N-alkylated N-Betsyl Amino Acid:

Dihydrofuran (90 mmol) and pyridinium p-toluenesulfonate (1.5 mmol) were added to a suspension of N-Betsyl amino acid (30 mmol) in dichloromethane (50 mL) at 0° C. The resulting mixture was stirred for 15 min at 0° C. and for 60 min at room temperature. The reaction mixture was diluted with diethyl ether (150 mL), washed with saturated aqueous sodium bicarbonate (20 mL), brine (20 mL), dried over magnesium sulfate, filtered and evaporated under reduced pressure to give the tetrahydrofuranyl ester of amino acid. A mixture of this ester (30 mmol), an alcohol (type D building block) (i.e. 4-(tert-butoxycarbonylamino)-cis-2-buten-1-ol, or 4-(tert-butoxycarbonylamino)-2-butyn-1-ol, or 5-(tert-butoxycarbonylamino)-trans-2-penten-1-ol)) (43.5 mmol) and triphenylphosphine (49 mmol) were suspended in toluene (20 mL) and azeotropically distilled three times in vacuum. The residue was dissolved in tetrahydrofuran (40 mL). Diisopropyl azodicarboxylate (43.5 mmol) was added at 0° C. After stirring for 15 min at 0° C. and for 30 min at room temperature, 1N hydrochloric acid (30 mL) and methanol (30 mL) was added and stirred for an additional 60 min. After removal of the organic solvents by evaporation, the aqueous phase was diluted with water (30 mL), the pH of the medium was adjusted to 12 with potassium carbonate, washed with diethyl ether (3×60 mL), and then acidified to pH 2-3 with 1N hydrochloric acid, extracted with dichloromethane (3×200 mL). The combined dichloromethane solution was washed with brine (100 mL), dried over magnesium sulfate, filtered and evaporated under reduced pressure to give the desired alkylated N-Betsyl amino acid in the overall yield of 68-89%.

What is claimed is:

1. A macrocyclic compound of formula I:

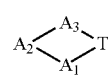

(I)

and pharmaceutically acceptable salts thereof, wherein $A_1$ is

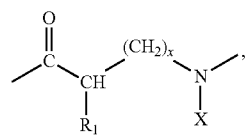

where the nitrogen is bonded to T and the carbonyl is bonded to $A_2$;

x is 0, 1 or 2;

23

$R_1$ is selected from the group consisting of:

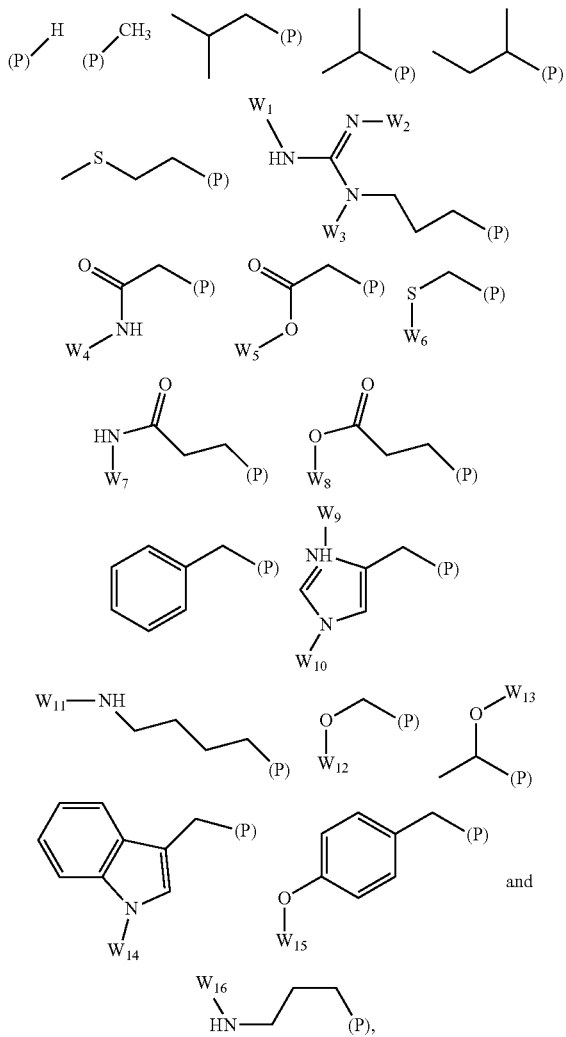

wherein (P) indicates the point of attachment to CH;

$W_1$ to $W_{16}$ are each independently hydrogen or a protecting group used for orthogonal protection in peptide synthesis; and X is selected from the group consisting of:

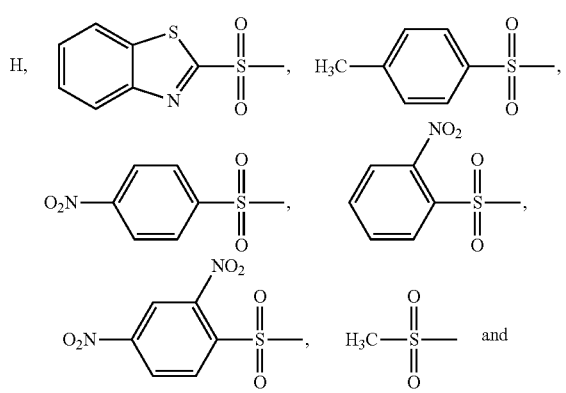

24

-continued

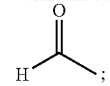

$A_2$ is selected from the group consisting of prolinyl, 4-hydroxyprolinyl, 4-tert-butoxyprolinyl; and

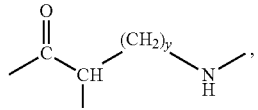

where the nitrogen is bonded to the carbonyl of $A_1$ and the carbonyl is bonded to $A_3$; wherein y is 0, 1 or 2;

$R_2$ is selected from the group consisting of:

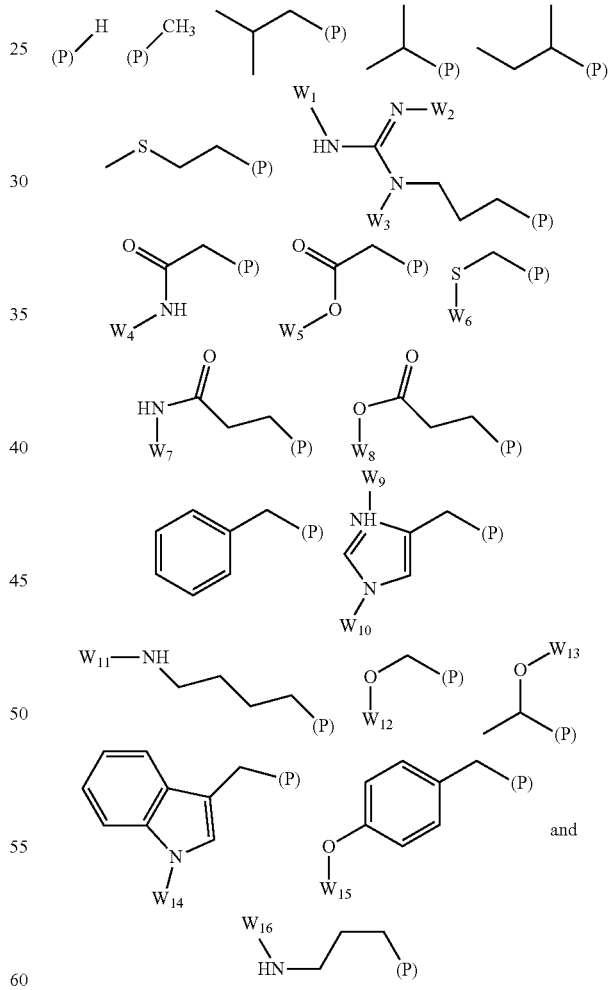

wherein (P) indicates the point of attachment to CH; and $W_1$ to $W_{16}$ are each independently hydrogen or a protecting group used for orthogonal protection in peptide synthesis;

$A_3$ is selected from the group consisting of prolinyl, 4-hydroxyprolinyl, 4-tert-butoxyprolinyl; and

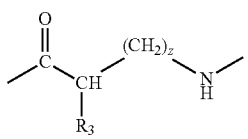

where the nitrogen is bonded to the carbonyl of $A_2$ and the carbonyl is bonded to T; wherein z is 0, 1 or 2;

$R_3$ is selected from the group consisting of:

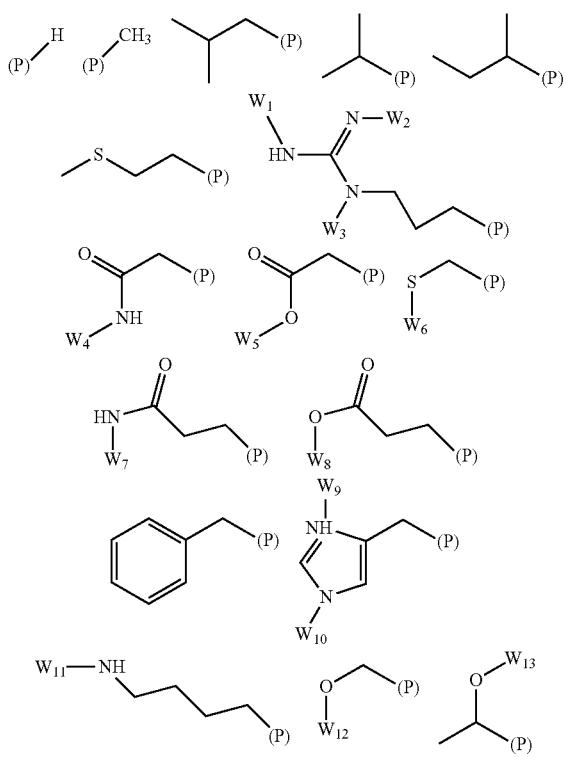

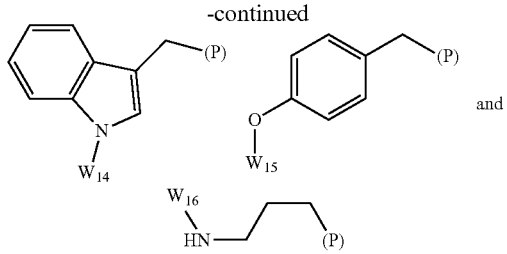

wherein (P) indicates the point of attachment to CH; and $W_1$ to $W_{16}$ are each independently hydrogen or a protecting group used for orthogonal protection in peptide synthesis; and (T) is selected from the group consisting of:

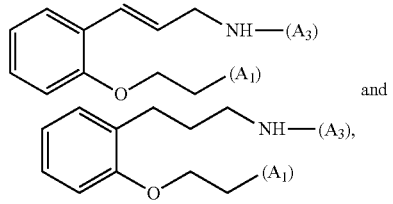

wherein ($A_3$) indicates the site of a covalent bond to $A_3$ of formula I and ($A_1$) indicates the site of a covalent bond to $A_1$ of formula I.

2. The macrocyclic compound of claim 1, wherein x, y and z are each independently 0 or 1, and X is H.

3. The macrocyclic compound of claim 2, wherein $R_1$, $R_2$ and $R_3$ are each independently

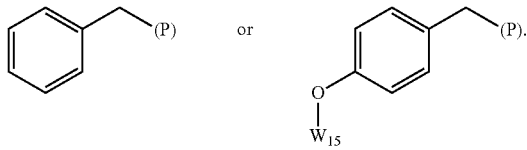

* * * * *